United States Patent [19]

McClelland et al.

[11] Patent Number: 5,756,086

[45] Date of Patent: *May 26, 1998

[54] ADENOVIRUSES HAVING MODIFIED FIBER PROTEINS

[75] Inventors: Alan McClelland, Gaithersburg; Susan C. Stevenson, Frederick, both of Md.

[73] Assignee: Genetic Therapy, Inc., Gaithersburg, Md.

[*] Notice: The term of this patent shall not extend beyond the expiration date of Pat. No. 5,543,328.

[21] Appl. No.: 591,492

[22] PCT Filed: Aug. 11, 1994

[86] PCT No.: PCT/US94/09172

§ 371 Date: Feb. 6, 1996

§ 102(e) Date: Feb. 6, 1996

[87] PCT Pub. No.: WO95/05201

PCT Pub. Date: Feb. 23, 1995

Related U.S. Application Data

[63] Continuation-in-part of Ser. No. 106,078, Aug. 13, 1993, Pat. No. 5,543,328.

[51] Int. Cl.⁶ .......................... C12N 15/86; C12N 15/62; C12N 15/34; A61K 48/00
[52] U.S. Cl. .................... 424/93.2; 435/69.1; 435/172.3; 435/320.1; 536/23.4; 536/23.72
[58] Field of Search ............................ 435/172.3, 320.1, 435/69.1; 424/93.2; 536/23.4, 23.72

[56] References Cited

U.S. PATENT DOCUMENTS

5,559,099   9/1996   Wickham et al. ............... 514/44

FOREIGN PATENT DOCUMENTS

WO 94/10323   5/1994   WIPO.

OTHER PUBLICATIONS

Bisbee, Genetic Engineering News 17(8):1 et seq (1997).
B.N. Fields et al., eds. *Fundamental Virology*, 2nd ed. New York: Raven Pres, 1991, p. 779.
"Report and Recommendations of the Panel to Assess the NIH Investment in Research on Gene Therapy," Orkin and Motulsky, Co–chairs, Dec. 7, 1995.
Levine et al., (1993) Am. J. Dis. Child 147(11):1167–1174.
Jolly, (1994) Cancer Gene Therapy 1(1):51–64.

*Primary Examiner*—Johnny F. Railey, II
*Attorney, Agent, or Firm*—Elliot M. Olstein; Raymond J. Lillie

[57] ABSTRACT

An adenovirus wherein the adenovirus fiber protein includes a ligand which is specific for a receptor located on a desired cell type. The adenovirus may have at least a portion of the adenovirus fiber protein removed and replaced with a ligand which is specific for a receptor located on a desired cell type, or the adenovirus may include a fusion protein of the adenovirus fiber protein and the ligand. Such an adenovirus may also include a gene(s) encoding a therapeutic agent(s) and may be "targeted" in order to deliver such gene(s) to a desired cell type.

14 Claims, 23 Drawing Sheets

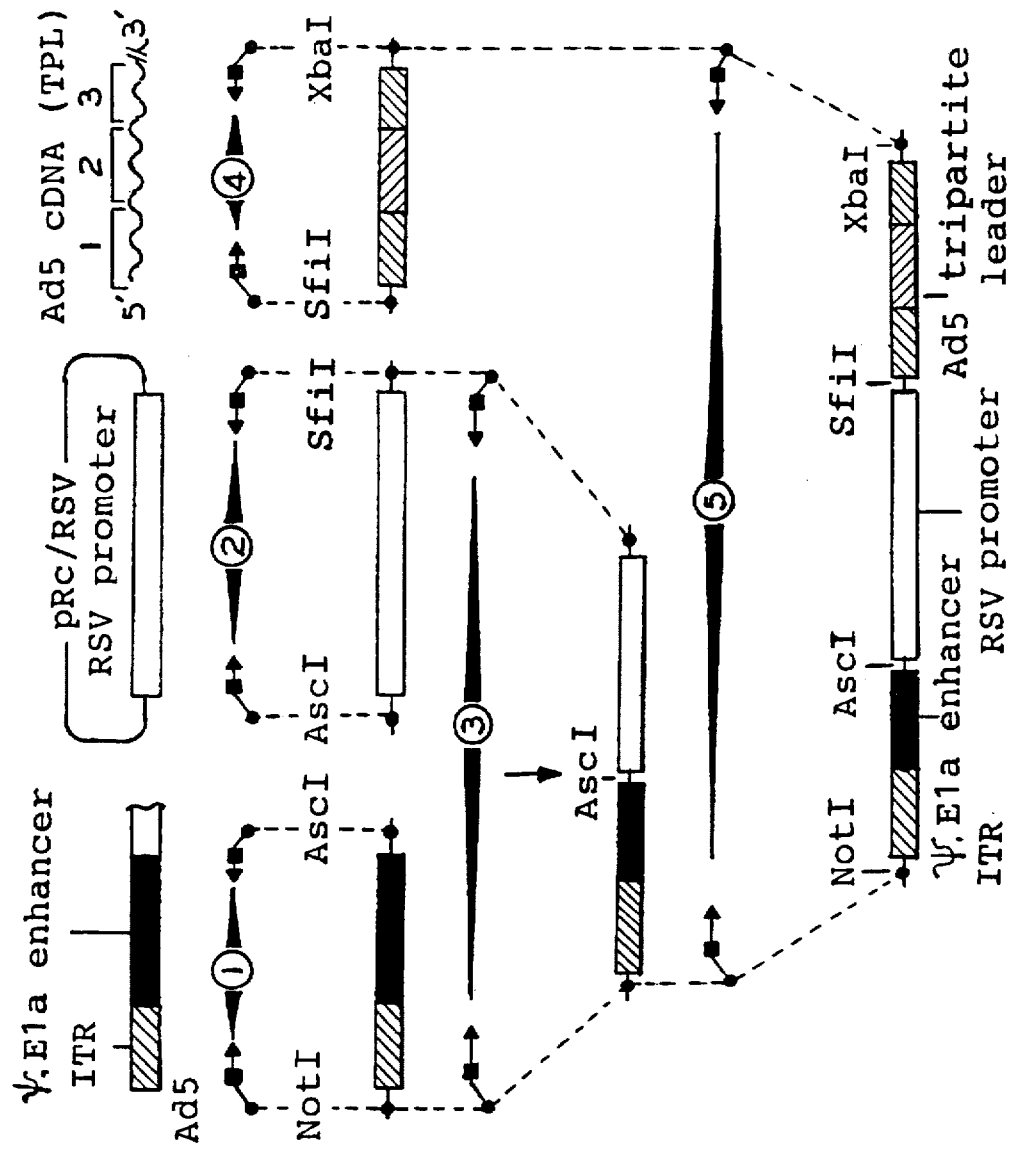
F I G. 7

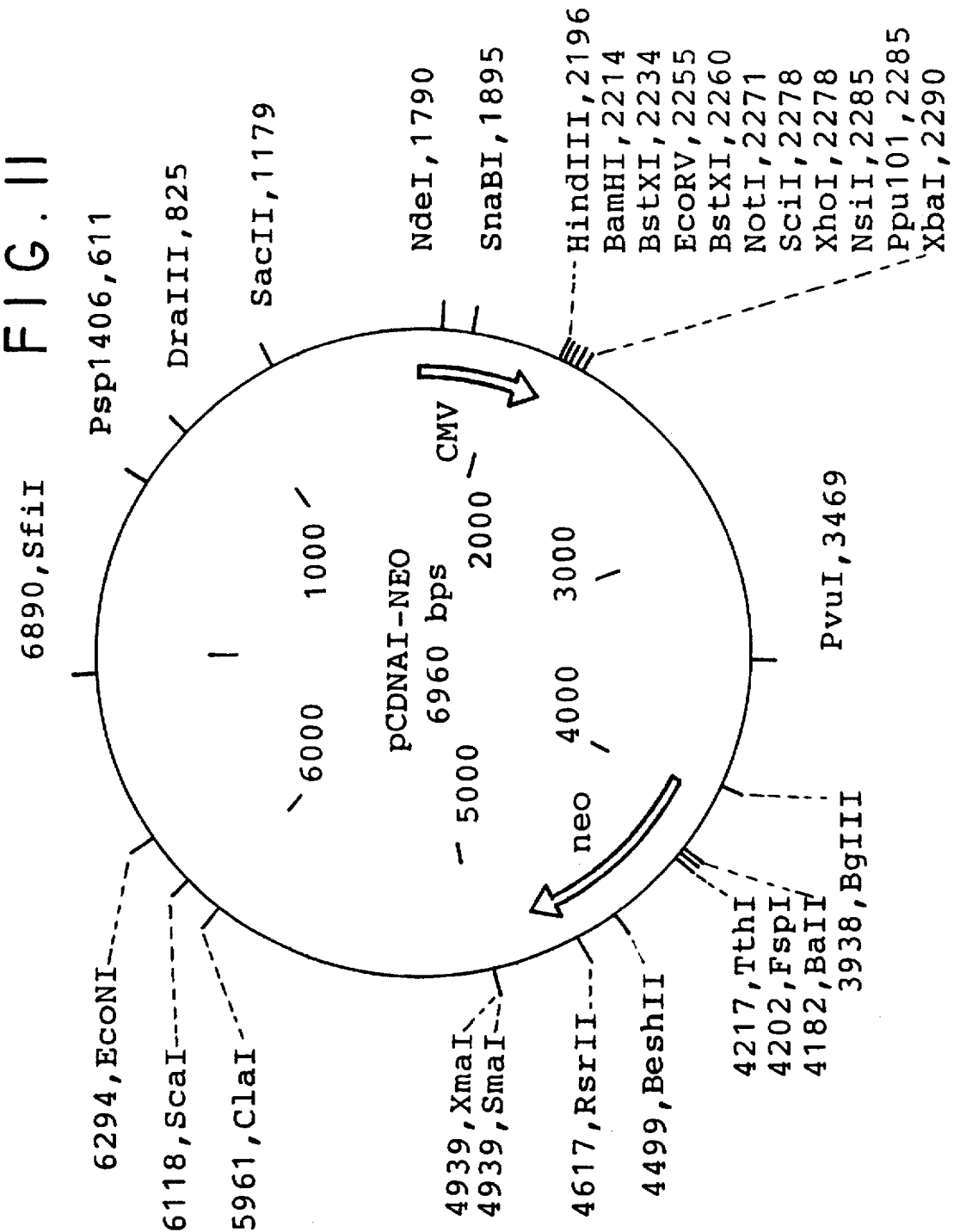

FIG. 20

```
   1  AGGTTATGCA GCGCGTGAAC ATGATCATGG CAGAATCACC AGGCCTCATC ACCATCTGC
  61  TTTTAGGATA TCTACTCAGT GCTGAATGTA CAGTTTTCT TGATCATGAA AACGCCAAC
 121  AAATTCTGAA TCGGCCAAAG AGGTATAATT CAGGTAAATT GGAAGAGTTT GTCAAGGG
 181  ACCTGAGAG AGAATGTATG GAAGAAAAGT GTAGTTTTGA AGAAGCACGA GAAGTTTT
 241  AAAACACTGA AAGAACAACT GAATTTTGGA AGCAGTATGT TGATGGAGAT CAGTGTGAG
 301  CCAATCCATG TTTAAATGGC GGCAGTGCA AGGATGACAT TAATTCCTAT GAATGTTGG
 361  GTCCCTTTGG ATTTGAAGGA AAGAACTGTG AATTAGATGT AACATGTAAC ATTAAGAAT
 421  GCAGATGCGA GCAGTTTTGT AAAAATAGTG CTGATAACAA GGTGGTTTGC TCCTGTACT
 481  AGGGATATCG ACTTGCAGAA AACCAGAAGT CCTGTGAACC AGCAGTGCCA TTTCCATGT
 541  GAAGAGTTTC TGTTTCACAA ACTTCTAAGC TCACCCGTGC TGAGACTGTT TTTCCTGAT
 601  TGGACTATGT AAATTCTACT GAAGCTGAAA CCATTTTGGA TAACATCACT CAAAGCACC
 661  AATCATTAA TGACTTCACT CGGGTTGTTG GTGGAGAAGA TGCCAAACCA GGTCAATTC
 721  CTTGGCAGGT TGTTTTGAAT GGTAAAGTTG ATGCATTCTG TGGAGGCTCT ATCGTTAAT
 781  AAAAATGGAT TGTAACTGCT GCCCACTGTG TTGAAACTGG TGTTAAAATT ACAGTTGTC
 841  CAGGTGAACA TAATATTGAG GAGACAGAAC ATACAGAGCA AAAGCGAAAT GTGATTCGA
 901  TTATTCCTCA CCACAACTAC AATGCAGCTA TTAATAAGTA CAACCATGAC ATTGCCCTT
 961  TGGAACTGGA CGAACCCTTA GTGCTAAACA GCTACGTTAC ACCTATTGC ATTGCTGAC
1021  AGGAATACAC GAACATCTTC CTCAAATTTG GATCTGGCTA TGTAAGTGGC TGGGGAAGA
1081  TCTTCCACAA AGGGAGATCA GCTTTAGTTC TTCAGTACCT TAGAGTTCCA CTTGTTGAC
1141  GAGCCACATG TCTTCGATCT ACAAAGTTCA CCATCTATAA CAACATGTTC TGTGCTGGC
1201  TCCATGAAGG AGGTAGAGAT TCATGTCAAG GAGATAGTGG GGGACCCCAT GTTACTGAA
1261  TGGAAGGGAC CAGTTTCTTA ACTGGAATTA TTAGCTGGGG TGAAGAGTGT GCAATGAAA
1321  GCAAATATGG AATATATACC AAGGTATCCC GGTATGTCAA CTGGATTAAG GAAAAAACA
1381  AGCTCACTTA ATGAAAGATG GATTCCAAG GTTAATTCAT TGGAATTGAA AATTAACAG
1441  GCCTCTCACT AACTAATCAC TTTCCCATCT TTTGTTAGAT TTGAATATAT ACATTCTAT
1501  ATCATTGCTT TTTCTCTTTA CAGGGGAGAA TTTCATATTT TACCTGAG
```

ADENOVIRUSES HAVING MODIFIED FIBER PROTEINS

This application is a 371 of PCT/U.S. 94/09172, filed Aug. 11,1994, continuation-in-part of application Ser. No. 08/106,078, filed Aug. 13, 1993, now U.S. Pat. No. 5,543,328.

This invention relates to adenoviruses as used as gene delivery vehicles. More particularly, this invention relates to adenoviruses having fiber proteins which are modified such that the fiber protein includes a ligand which enables the adenovirus to be targeted to a desired cell type.

BACKGROUND OF THE INVENTION

Adenovirus genomes are linear, double-stranded DNA molecules about 36 kilobase pairs long. Each extremity of the viral genome has a short sequence known as the inverted terminal repeat (or ITR), which is necessary for viral replication. The well-characterized molecular genetics of adenovirus render it an advantageous vector for gene transfer. The knowledge of the genetic organization of adenoviruses allows substitution of large fragments of viral DNA with foreign sequences. In addition, recombinant adenoviruses are structurally stable and no rearranged viruses are observed after extensive amplification.

Adenoviruses may be employed as delivery vehicles for introducing desired genes into eukaryotic cells. The adenovirus delivers such genes to eukaryotic cells by binding cellular receptors. The adenovirus fiber protein is responsible for such attachment. (Philipson, et al., *J. Virol.*, Vol. 2, pgs. 1064–1075 (1968)). The fiber protein consists of two domains—a rod-like shaft portion and a globular head portion which contains the putative receptor binding region. The fiber spike is a homotrimer, and there are 12 spikes per virion. Human adenoviruses may bind to and infect a broad range of cultured cell lines and primary tissues from different species.

It is an object of the present invention to provide an adenovirus which can be targeted to a desired cell type.

DETAILED DESCRIPTION OF THE INVENTION

In accordance with an aspect of the present invention, there is provided an adenovirus wherein the adenovirus fiber includes a ligand which is specific for a receptor located on a desired cell type.

In one embodiment, at least a portion of the adenovirus fiber protein is removed and replaced with a ligand which is specific for a receptor located on a desired cell type. In such embodiments the natural adenoviral ligand is removed and replaced with a ligand which is specific for a receptor located on a desired cell type.

As stated hereinabove, the adenovirus fiber protein includes a head portion and a shaft portion. In one embodiment, at least a portion of the head portion is removed and replaced with a ligand which is specific for a receptor located on a desired cell type. In one embodiment, a portion of the head portion is removed and replaced with a ligand which is specific for a receptor located on a desired cell type. In another embodiment, all of the head portion is removed and replaced with a ligand which is specific for a receptor located on a desired cell type.

In one embodiment, the adenovirus is Adenovirus 3, and amino acid residues 132 to 319 of the fiber (i.e., the fiber head region) of Adenovirus 3 are removed and are replaced with a ligand which is specific for a receptor located on a desired cell type. The DNA encoding the fiber protein of Adenovirus 3 is registered as Genbank accession #M12411, (incorporated herein by reference). In another embodiment, the adenovirus is Adenovirus 5, and amino acid residues 400 to 581 of the fiber (i.e., the fiber head region) of Adenovirus 5 are removed and are replaced with a ligand. The DNA encoding the fiber protein of Adenovirus 5 is registered as Genbank accession #M18369, (incorporated herein by reference). In yet another embodiment, the adenovirus is Adenovirus 41, and amino acid residues 387 to 563 of the long fiber (i.e., the fiber head region) of Adenovirus 41 are removed and replaced with a ligand. In a further embodiment, the adenovirus is Adenovirus 41, and amino acid residues 231 to 387 of the short fiber (i.e., the fiber head region) of Adenovirus 41 short are removed and replaced with a ligand. The DNA encoding the Adenovirus 41 long and short fibers is registered as Genbank accession #X17016, incorporated herein by reference.

Ligands which may replace a portion of the adenovirus fiber protein include, but are not limited to, the TNF superfamily of ligands which include tumor necrosis factors (or TNF's) such as, for example, TNF-alpha and TNF-beta, lymphotoxins (LT), such as LT-α and LT-β, Fas ligand which binds to Fas antigen; CD40 ligand, which binds to the CD40 receptor of B-lymphocytes; CD30 ligand, which binds to the CD30 receptor of neoplastic cells of Hodgkin's lymphoma; CD27 ligand, NGF ligand, and OX-40 ligand; transferrin, which binds to the transferrin receptor located on tumor cells, activated T-cells, and neural tissue cells; ApoB, which binds to the LDL receptor of liver cells; alpha-2-macroglobulin, which binds to the LRP receptor of liver cells; alpha-1 acid glycoprotein, which binds to the asialoglycoprotein receptor of liver; mannose-containing peptides, which bind to the mannose receptor of macrophages; sialyl-Lewis-X antigen-containing peptides, which bind to the ELAM-1 receptor of activated endothelial cells; CD34 ligand, which binds to the CD34 receptor of hematopoietic progenitor cells; ICAM-1, which binds to the LFA-1 (CD11b/CD18) receptor of lymphocytes, or to the Mac-1 (CD11a/CD18) receptor of macrophages; M-CSF, which binds to the c-fms receptor of spleen and bone marrow macrophages; circumsporozoite protein, which binds to hepatic *Plasmodium falciparum* receptor of liver cells; VLA-4, which binds to the VCAM-1 receptor of activated endothelial cells; LFA-1, which binds to the ICAM-1 receptor of activated endothelial cells; NGF, which binds to the NGF receptor of neural cells; HIV gp1120 and Class II MHC antigen, which bind to the CD4 receptor of T-helper cells; the LDL receptor binding region of the apolipoprotein E (ApoE) molecule; colony stimulating factor, or CSF, which binds to the CSF receptor; insulin-like growth factors, such as IGF-I and IGF-II, which bind to the IGF-I and IGF-II receptors, respectively; Interleukins 1 through 14, which bind to the Interleukin 1 through 14 receptors, respectively; and the Fv antigen-binding domain of an immunoglobulin.

In a preferred embodiment, because the adenovirus fiber has a trimeric structure, the ligand which replaces at least a portion of the adenovirus fiber also has a trimeric structure. In a more preferred embodiment, the ligand is selected from the TNF superfamily of ligands hereinabove described. Such ligands are trimeric and of similar size to the fiber head domain. Such ligands are described further in Beutler, et al., *Science*, Vol. 264, pgs. 667–668 (Apr. 29, 1994).

Such adenoviruses may be constructed from adenoviral vectors wherein DNA encoding a portion of the fiber protein of the adenovirus is removed and is replaced with DNA encoding a ligand which is specific for a receptor located on a desired cell type.

In another embodiment, the adenovirus includes a fusion protein of the adenovirus fiber protein and a ligand which is specific for a receptor located on a desired cell type.

Adenovirus fiber proteins which may be included in the fusion protein include, but are not limited to, the Adenovirus 3 fiber protein, the Adenovirus 5 fiber protein, and the Adenovirus 41 long and short fiber proteins. The adenovirus fiber protein may be the complete native fiber protein, or may be a mutated fiber protein. The term "mutated" as used herein means that at least one and no more than 100 amino acid residues of the native adenovirus fiber protein have been changed, or that at least one and no more than 100 amino acid residues of the native adenovirus fiber protein have been deleted from the native adenovirus fiber protein.

Ligands may be selected from those hereinabove described.

Such adenoviruses may be vectors wherein DNA encoding the native or mutated adenoviral fiber protein hereinabove mentioned is fused (i.e., operatively linked) to DNA encoding the ligand.

The adenoviral vector, in general, also includes DNA encoding at least one therapeutic agent. The term "therapeutic" is used in a generic sense and includes treating agents, prophylactic agents, and replacement agents.

DNA sequences encoding therapeutic agents which may be placed into the adenoviral vector include, but are not limited to, DNA sequences encoding tumor necrosis factor (TNF) genes, such as TNF-α; genes encoding interferons such as Interferon-α, Interferon-β, and Interferon-γ; genes encoding interleukins such as IL-1, IL-1β, and Interleukins 2 through 14; genes encoding GM-CSF; genes encoding adenosine deaminase, or ADA; genes which encode cellular growth factors, such as lymphokines, which are growth factors for lymphocytes; genes encoding soluble CD4; Factor VIII; Factor IX; T-cell receptors; the LDL receptor, ApoE, ApoC,ApoAI and other genes involved in cholesterol transport and metabolism; the alpha-1 antitrypsin (α1AT) gene, the ornithine transcarbamylase (OTC) gene, the CFTR gene, the insulin gene, negative selective markers or "suicide" genes, such as viral thymidine kinase genes, such as the Herpes Simplex Virus thymidine kinase gene, the cytomegalovirus virus thymidine kinase gene, and the varicella-zoster virus thymidine kinase gene; Fc receptors for antigen-binding domains of antibodies, and antisense sequences which inhibit viral replication, such as antisense sequences which inhibit replication of hepatitis B or hepatitis non-A non-B virus.

The DNA sequence encoding at least one therapeutic agent is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; and the ApoAI promoter. It is to be understood, however, that the scope of the present invention is not to be limited to specific foreign genes or promoters.

The adenoviral vector which is employed may, in one embodiment, be an adenoviral vector which includes essentially the complete adenoviral genome. (Shenk, et al., *Curr. Top. Microbiol. Immunol.*, (1984); 111(3):1–39), incorporated herein by reference. Alternatively, the adenoviral vector may be a modified adenoviral vector in which at least a portion of the adenoviral genome has been deleted.

In one embodiment, the vector comprises an adenoviral 5' ITR; an adenoviral 3' ITR; an adenoviral encapsidation signal; at least one DNA sequence encoding a therapeutic agent(s); and a promoter controlling the DNA sequence(s) encoding a therapeutic agent(s). The vector is free of at least the majority of adenoviral E1 and E3 DNA sequences, but is not free of all of the E2 and E4 DNA sequences, and DNA sequences encoding adenoviral proteins promoted by the adenoviral major late promoter. In one embodiment, the vector is also free of at least a portion of at least one DNA sequence selected from the group consisting of the E2 and E4 DNA sequences. In another embodiment, the vector is free of at least the majority of the adenoviral E1 and E3 DNA sequences, and is free of one of the E2 and E4 DNA sequences, and is free of a portion of the other of the E2 and E4 DNA sequences.

In yet another embodiment, the vector is free of at least the majority of the E1 and E3 DNA sequences, is free of at least a portion of at least one DNA sequence selected from the group consisting of the E2 and E4 DNA sequences, and is free of DNA sequences encoding adenoviral proteins promoted by the adenoviral major late promoter.

Such a vector, in a preferred embodiment, is constructed first by constructing, according to standard techniques, a shuttle plasmid which contains, beginning at the 5' end, the "critical left end elements," which include an adenoviral 5' ITR, an adenoviral encapsidation signal, and an E1a enhancer sequence; a promoter (which may be an adenoviral promoter or a foreign promoter); a tripartite leader sequence, a multiple cloning site (which may be as hereinabove described); a poly A signal; and a DNA segment which corresponds to a segment of the adenoviral genome. Such DNA segment serves as a substrate for homologous recombination with a modified or mutated adenovirus, and such sequence may encompass, for example, a segment of the adenovirus 5 genome no longer than from base 3329 to base 6246 of the genome. The plasmid may also include a selectable marker and an origin of replication. The origin of replication may be a bacterial origin of replication. Representative examples of such shuttle plasmids include pAVS6, shown in FIG. 9. A desired DNA sequence encoding a therapeutic agent may then be inserted into the multiple cloning site. Homologous recombination is then effected with a modified or mutated adenovirus in which at least the majority of the E1 and E3 adenoviral DNA sequences have been deleted. Such homologous recombination may be effected through co-transfection of the shuttle plasmid and the modified adenovirus into a helper cell line, such as 293 cells, by $CaPO_4$ precipitation. Upon such homologous recombination, a recombinant adenoviral vector is formed which includes DNA sequences derived from the shuttle plasmid between the Not I site and the homologous recombination fragment, and DNA derived from the E1 and E3 deleted adenovirus between the homologous recombination fragment and the 3' ITR.

In one embodiment, the homologous recombination fragment overlaps with nucleotides 3329 to 6246 of the adenovirus 5 genome.

Through such homologous recombination, a vector is formed which includes an adenoviral 5' ITR, an adenoviral encapsidation signal; an E1a enhancer sequence; a promoter; a tripartite leader sequence; at least one DNA sequence encoding a therapeutic agent; a poly A signal; adenoviral DNA free of at least the majority of the E1 and E3 adenoviral DNA sequences; and an adenoviral 3' ITR. This vector may then be transfected into a helper cell line, such as the 293 helper cell line, which will include the E1a and E1b DNA sequences, which are necessary for viral replication, and to generate infectious viral particles.

The vector is transfected into an appropriate cell line for the generation of infectious viral particles wherein the adenovirus fiber includes a ligand which is specific for a receptor located on a desired cell type. Transfection may take place by electroporation, calcium phosphate precipitation, microinjection, or through proteoliposomes.

Examples of appropriate cell lines include, but are not limited to, HeLa cells or 293 (embryonic kidney epithelial) cells. In another embodiment, the adenoviral vector comprises an adenoviral 5' ITR; an adenoviral 3' ITR; an adenoviral encapsidation signal; at least one DNA sequence encoding a therapeutic agent; and a promoter controlling the at least one DNA sequence encoding a therapeutic agent. The vector is free of the adenoviral E1, E2, E3, and E4 DNA sequences, and the vector is free of DNA sequences encoding adenoviral proteins promoted by the adenoviral major late promoter; i.e., the vector is free of DNA encoding adenoviral structural proteins.

Such vectors may be constructed by removing the adenoviral 5' ITR, the adenoviral 3' ITR, and the adenoviral encapsidation signal, from an adenoviral genome by standard techniques. Such components, as well as a promoter (which may be an adenoviral promoter or a non-adenoviral promoter), tripartite leader sequence, poly A signal, and selectable marker, may, by standard techniques, be ligated into a base plasmid or "starter" plasmid such as, for example, pBluescript II KS-(Stratagene), to form an appropriate cloning vector. The cloning vector may include a multiple cloning site to facilitate the insertion of DNA sequence(s) encoding therapeutic agent(s) into the cloning vector. In general, the multiple cloning site includes "rare" restriction enzyme sites; i.e., sites which are found in eukaryotic genes at a frequency of from about one in every 10,000 to about one in every 100,000 base pairs. An appropriate vector is thus formed by cutting the cloning vector by standard techniques at appropriate restriction sites in the multiple cloning site, and then ligating the DNA sequence encoding a therapeutic agent(s) into the cloning vector.

The vector may then be packaged into infectious viral particles using a helper adenovirus which provides the necessary encapsidation materials. Preferably the helper virus has a defective encapsidation signal in order that the helper virus will not encapsidate itself. An example of an encapsidation defective helper virus which may be employed is described in Grable, et al., *J. Virol.*, Vol. 66, pgs. 723–731 (1992).

In one embodiment, the adenovirus having a modified fiber may be constructed by using a yeast artificial chromosome (or YAC) containing an adenoviral genome. In this embodiment, the adenovirus yeast artificial chromosome is produced by homologous recombination in vivo between adenoviral DNA and yeast artificial chromosome plasmid vectors carrying segments of the adenoviral left and right genomic termini. The adenoviral DNA encoding the adenovirus fiber then may be modified such that at least a portion of the adenoviral DNA encoding the adenoviral fiber is removed and replaced with DNA encoding a ligand which is specific for a receptor which is located on a desired cell type. A gene(s) encoding a therapeutic agent(s) also may be cloned into the adenoviral DNA. The modified adenoviral genome then is excised from the adenovirus yeast artificial chromosome in order to be used to generate infectious adenoviral particles as hereinabove described.

The infectious viral particles may then be administered in vivo to a host. The host may be an animal host, including mammalian hosts and human hosts. Such viral particles are "targetable," i.e., the viral particles, upon administration to the host, will bind to and infect a desired target cell or tissue, and thereby delivering DNA encoding a therapeutic agent to the desired target cell or tissue. The particular target cell or tissue to which the particles are targeted is dependent upon the ligand with which the particle is engineered.

The targetable vector particle, which consists of an infectious adenovirus particle having a modified fiber protein, is administered in an amount effective to provide a therapeutic effect in a host. In one embodiment, the vector may be administered in an amount of from 1 plaque forming unit to about $10^{14}$ plaque forming units, preferably from about $10^6$ plaque forming units to about $10^{13}$ plaque forming units. The host may be a human or non-human animal host.

Preferably, the infectious vector particles are administered systemically, such as, for example, by intravenous administration (such as, for example, portal vein injection or peripheral vein injection), intramuscular administration, intraperitoneal administration, or intranasal administration.

The vector particles may be administered in combination with a pharmaceutically acceptable carrier suitable for administration to a patient. The carrier may be a liquid carrier (for example, a saline solution), or a solid carrier, such as, for example, microcarrier beads.

The vector particles, which include a fiber which is engineered with a ligand which is specific for a receptor located on a desired cell type, travel directly to the desired cells or tissues upon the in vivo administration of such vector particles to a host, and whereby such vector particles infect the desired cell or tissues.

Cells which may be infected by the infectious viral particles include, but are not limited to, primary cells, such as primary nucleated blood cells, such as leukocytes, granulocytes, monocytes, macrophages, lymphocytes (including T-lymphocytes and B-lymphocytes), totipotent stem cells, and tumor infiltrating lymphocytes (TIL cells); bone marrow cells; endothelial cells; activated endothelial cells; epithelial cells; keratinocytes; stem cells; hepatocytes, including hepatocyte precursor cells; fibroblasts; mesenchymal cells; mesothelial cells; parenchymal cells; vascular smooth muscle cells; brain cells and other neural cells; gut enterocytes; gut stem cells; and myoblasts. The cell which is "targeted" or infected or transduced with the infectious viral particles is dependent upon the ligand with which the infectious viral particle has been engineered.

In one embodiment, the infectious viral particles may be targeted to blood cells, whereby such vector particles infect the blood cells with a gene which directly or indirectly enhances the therapeutic effects of the blood cells. The gene carried by the blood cells can be any gene which allows the blood cells to exert a therapeutic effect that it would not ordinarily have, such as a gene encoding a clotting factor useful in the treatment of hemophilia. The gene can encode one or more products having therapeutic effects. Examples of suitable genes include those that encode cytokines such as TNF, interleukins (interleukins 1–14), interferons (α, β, γ-interferons), T-cell receptor proteins and Fc receptors for antigen-binding domains of antibodies, such as immunoglobulins. Other examples of suitable genes include genes encoding soluble CD4 which is used in the treatment of AIDS and genes encoding α-antitrypsin, which is useful in the treatment of emphysema caused by α-antitrypsin deficiency.

The infected cells are useful in the treatment of a variety of diseases including but not limited to adenosine deaminase deficiency, sickle cell anemia, thalassemia, hemophilia, diabetes, α-antitrypsin deficiency, brain disorders such as Alzheimer's disease, phenylketonuria and other illnesses such as growth disorders and heart diseases, for example, those caused by alterations in the way cholesterol is metabolized and defects of the immune system.

In another embodiment, the vector particles may be targeted to and infect liver cells, and such vector particles may include gene(s) encoding polypeptides or proteins which are useful in prevention and therapy of an acquired or an inherited defect in hepatocyte (liver) function. For example, they can be used to correct an inherited deficiency of the low density lipoprotein (LDL) receptor, and/or to correct an inherited deficiency of ornithine transcarbamylase (OTC), which results in congenital hyperammonemia.

In another embodiment, the viral particles may be targeted to liver cells, whereby the viral particles include a gene encoding a therapeutic agent employed to treat acquired infectious diseases, such as diseases resulting from viral infection. For example, the infectious viral particles may be employed to treat viral hepatitis, particularly hepatitis B or non-A non-B hepatitis. For example, an infectious viral particle containing a gene encoding an anti-sense gene could be employed to infect liver cells to inhibit viral replication. In this case, the infectious viral particle, which includes a vector including a structural hepatitis gene in the reverse or opposite orientation, would be introduced into liver cells, resulting in production in the infected liver cells of an anti-sense gene capable of inactivating the hepatitis virus or its RNA transcripts. Alternatively, the liver cells may be infected with an infectious viral particle including a vector which includes a gene which encodes a protein, such as, for example, α-interferon, which may confer resistance to the hepatitis virus.

The present invention is particularly applicable to the treatment of Hodgkin's lymphoma. An infectious targetable adenoviral particle in accordance with the present invention may include CD30 ligand, which binds to the CD30 antigen or CD30 receptor, which is a surface marker for neoplastic cells of Hodgkin's lymphoma (Smith, et al., Cell, Vol. 73, pgs. 1349–1360 (Jul. 2, 1993); Durkop, et al., Cell, Vol. 68, pgs. 421–427 (Feb. 7, 1992); Renner, et al., Science, Vol. 264, pgs. 833–835 (May 6, 1994)). The targetable virus also includes a negative selective marker, or "suicide" gene, such as the Herpes Simplex thymidine kinase gene. The targetable adenovirus then may be administered in vivo to a patient, whereby the virus is targeted to and infects neoplastic cells of Hodgkin's lymphoma. After the targetable adenovirus is administered to the patient, the patient is given an interaction agent such as gancyclovir or aciclovir, whereby the neoplastic Hodgkin's lymphoma cells infected with the targetable adenovirus are killed.

Alternatively, the vector particles including the modified adenovirus fiber and a gene encoding a desired protein or therapeutic agent may be employed to infect a desired cell line in vitro, whereby the infected cells produce a desired protein or therapeutic agent in vitro.

BRIEF DESCRIPTION OF THE DRAWINGS

The invention will now be described with respect to the drawings, wherein:

FIG. 7 is a schematic of the construction of a construct including an adenoviral ITR, an encapsidation signal, an E1a enhancer sequence, a Rous Sarcoma Virus promoter, and an Adenovirus 5 tripartite leader sequence;
FIG. 10 is a map of plasmid pAVS5F::TNF;
FIG. 11 is a map of plasmid pcDNA-neo;
FIG. 20 is the DNA sequence encoding Factor IX(SEQ ID NO:21)

EXAMPLES

The invention will now be described with respect to the following examples; it is to be understood, however, that the scope of the present invention is not intended to be limited thereby.

Example 1

Construction of Adenovirus 5

Including a Chimeric Fiber of

Adenovirus 5 Fiber Protein and TNF

A. Construction of Vector Including DNA Encoding the Adenovirus 5 Fiber: TNF Chimera The Adenovirus 5 fiber: TNF (5F: TNF) chimera is prepared by PCR gene overlap extension (Horton et al. (1990) *Biotechniques* 8:528–535, incorporated herein by reference). The Adenovirus 5 fiber tail and shaft regions, amino acids 1 to 399, are connected with the mature TNF protein, amino acids 76 to 233. The primers which are used in the PCR construction are as follows:

5F P1 5'-CATTGTGTCGACACCATGAAGCGCGC
AAGACCGTCTGAA-3' (SEQ ID NO:1)

P2 5'-CGGGGTTCGAGAAGATGATCTGACGGTC
CACAAAGTTAGCTTATCATT-3' (SEQ ID NO:2)

TNF P3 5'-GTCAGATCATCTTCTCGAACCCCG-3'
(SEQ ID NO:3)

P4 5'-ATGTCTAGATCACAGGGCAATGATCCCA
AAGTAGACCTG-3' (SEQ ID NO:4)

Figure 1:
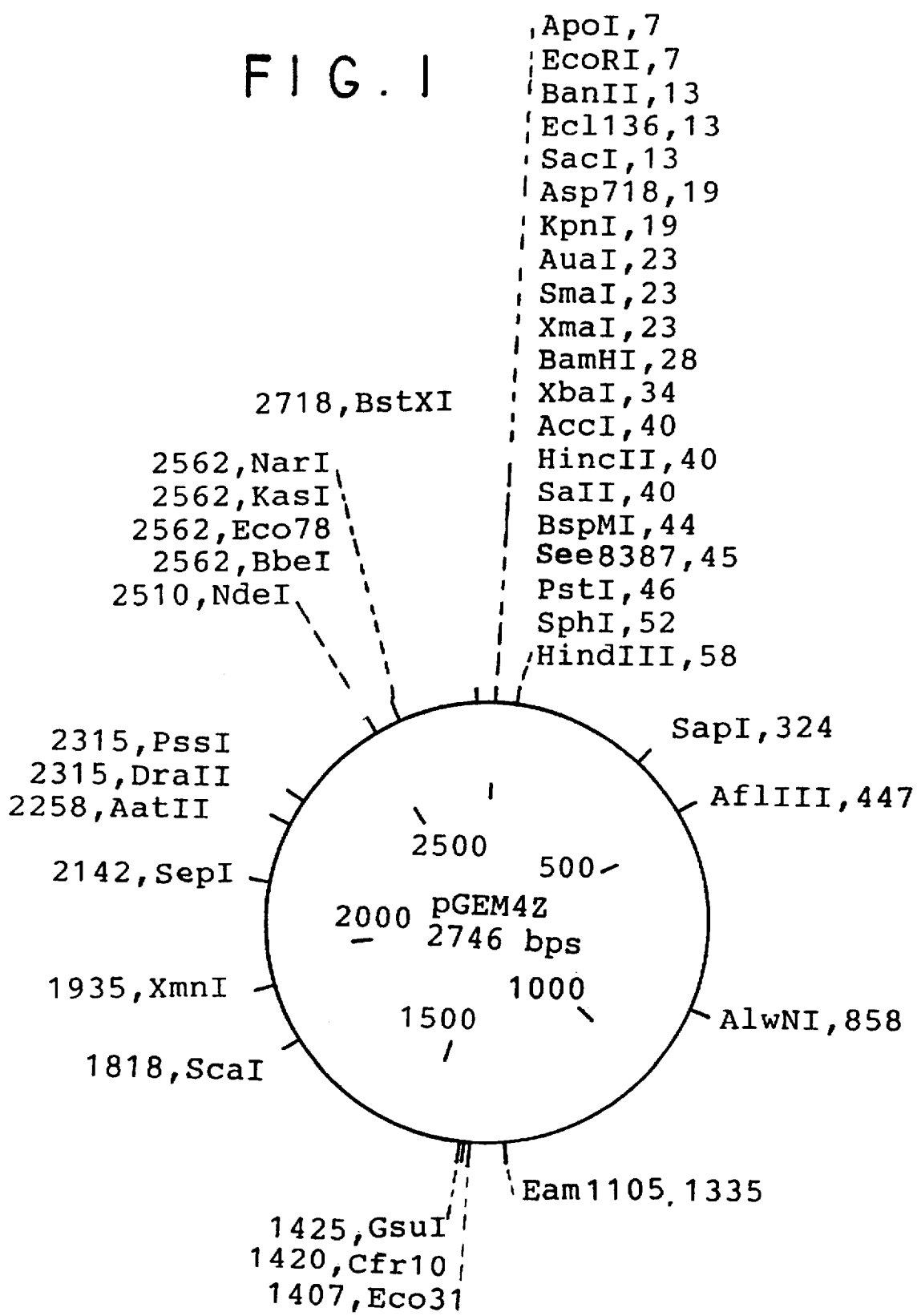
FIG. 1 is a map of the plasmid pGEM4Z.

The primers P1 and P2 amplify nucleotides 476 to 1684 of the Adenovirus 5 fiber sequence, Genbank #M18369, incorporated herein by reference. The primers P3 and P4 amplify nucleotides 314 to 787 of the human TNF sequence, Genbank #M10988, incorporated herein by reference. The primers P1 and P4 are designed to add Sal I and XbaI restriction enzyme sites, respectively, for cloning into the expression vector, pGEM4Z. (Promega, FIG. 1) The templates, pGEM5F (FIG. 2) and pT2 (FIG. 4), which contain the correct cDNA for the Adenovirus 5 fiber and human TNF genes, respectively, are used for amplifying the appropriate sequences.

The full length Adenovirus 5 fiber gene was cloned by PCR using the published DNA sequences (Chrobaczek, et al., (1989), Virology, Vol. 161, pgs. 549–554, incorporated herein by reference) to design oligonucleotide primers for amplification from purified genomic DNA. The primers were designed to amplify the entire coding sequence of the full length fiber gene starting from the start codon, ATG, and ending with the termination codon, TAA. The primers, designated, P5 and P6, are as follows:

P5 5'-CATCTGCAGCATGAAGCGCGCAAGACCG TCTGAAGATA-3' (SEQ ID NO:5)

P6 5'-CAGGAATTCTTATTCTTGGGCAATGTATG AAAAAGTGT-3' (SEQ ID NO:6)

Figure 2:
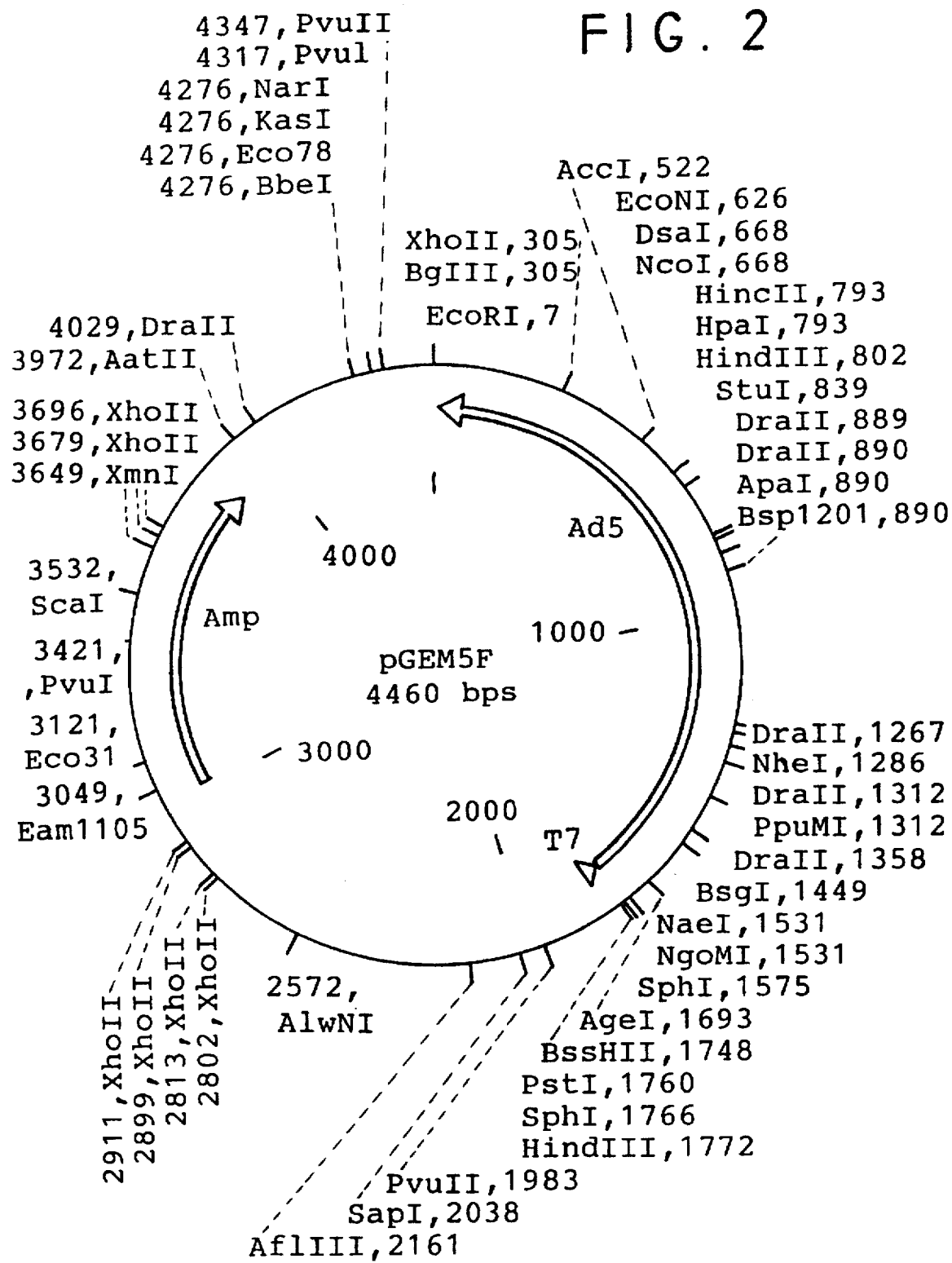
FIG. 2 is a map of the plasmid pGEM5F.

The primers P5 and P6 were designed to contain PstI and EcoRI restriction enzyme sites, respectively, for cloning into the plasmid pGEM4Z. The PCR reaction was carried out as follows: 5 min. -92° C.; then 45 sec. -92° C.; 45 sec. -52° C.; 2 min. -72° C. for 20 cycles, and then 8 min. -72° C. The PCR product then was cut with PstI and EcoRI, and cloned into PstI and EcoRI digested pGEM4Z to form pGEM5F (FIG. 2.).

pT2 is formed by cloning the human TNF gene by PCR using primers P7 and P8:

P7 5'-GCAGATCTTTCCGCAGCAGCCGCCACCA TGAGCATGAAAGCATC-3' (SEQ ID NO:7)

Figure 3:
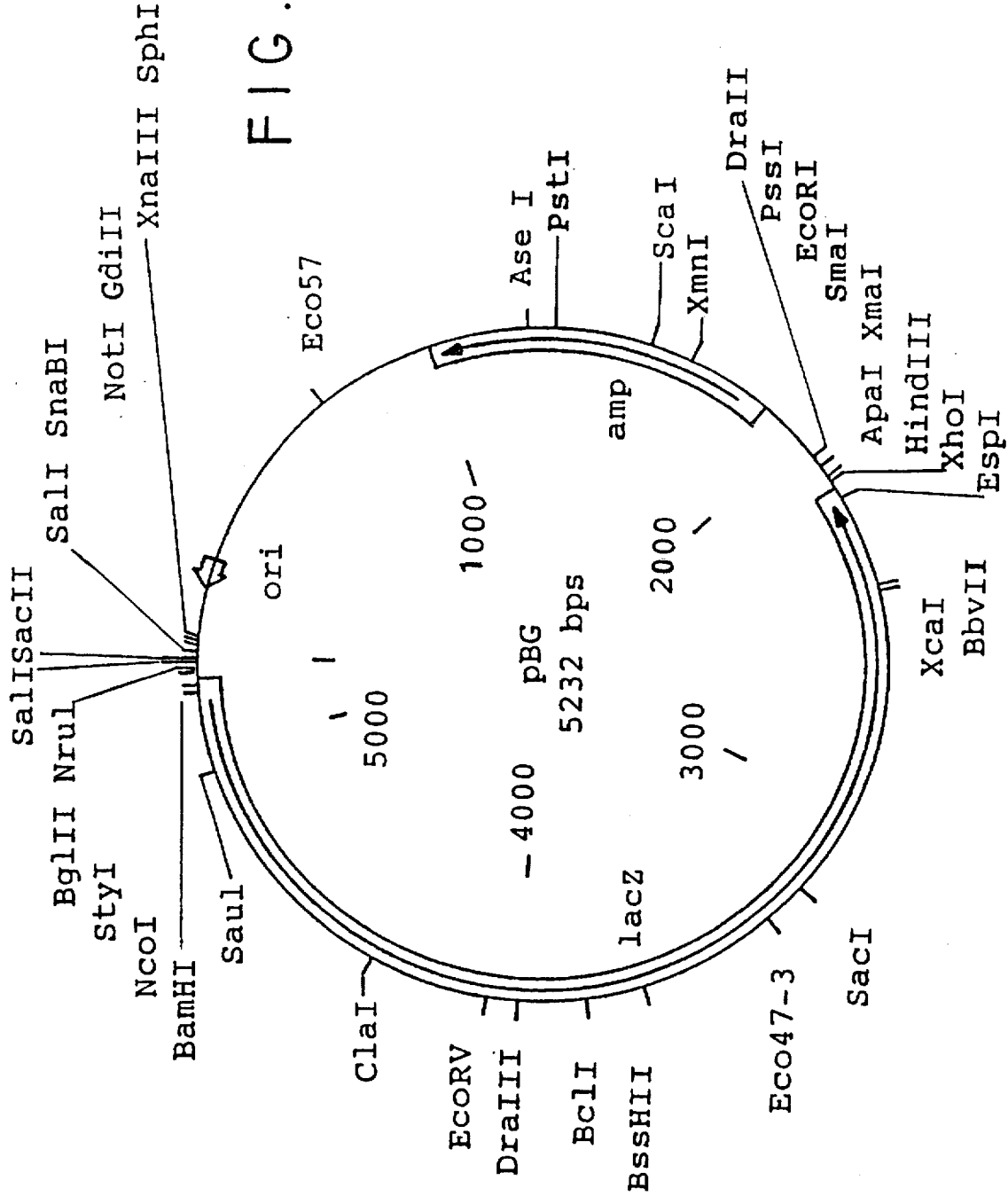
FIG. 3 is a map of the plasmid pBg.
Figure 4:
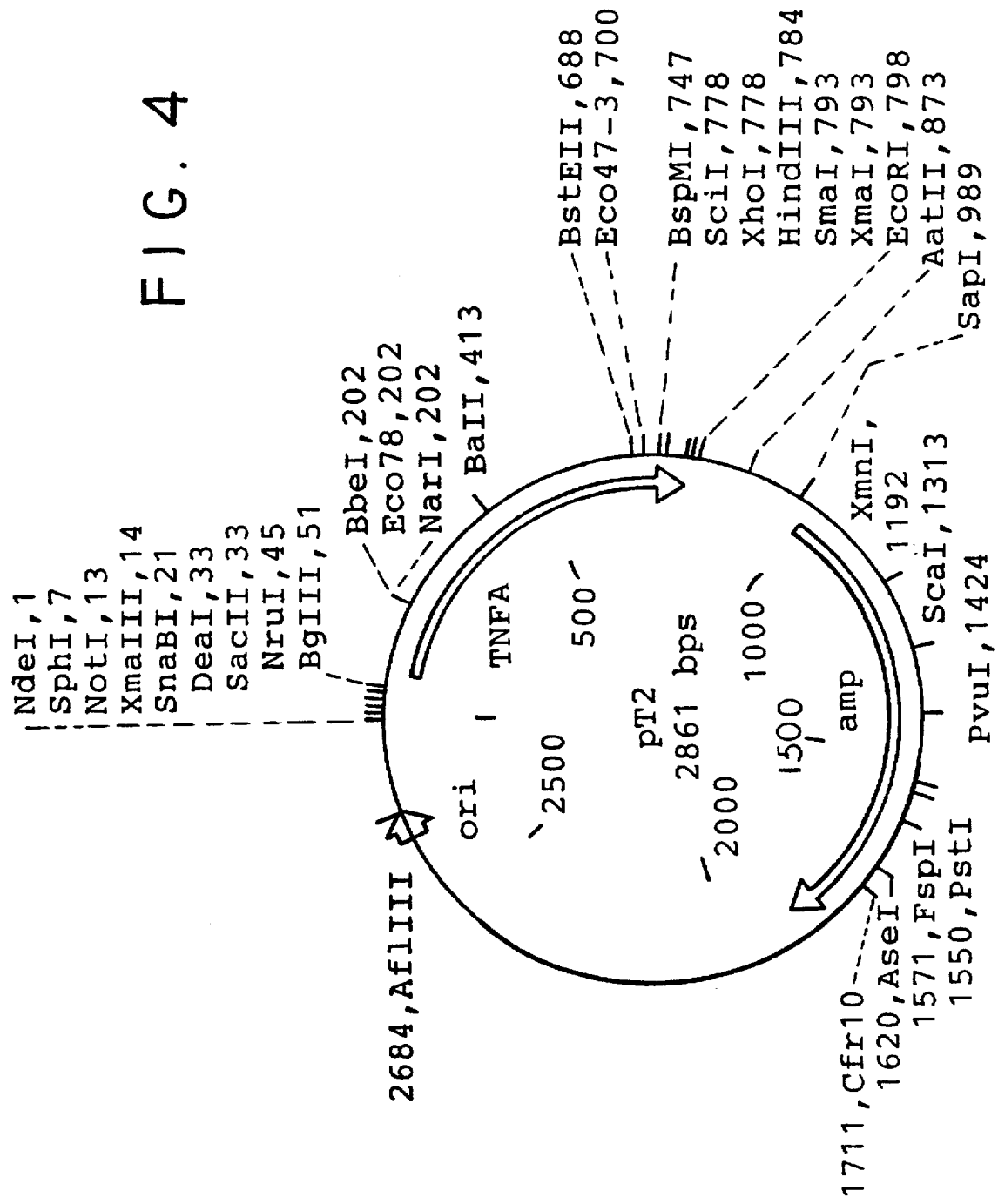
FIG. 4 is a map of the plasmid pT2.

P8 5'-GCGTCGACTCGAGTCACAGGGCAATGATCC-3' (SEQ ID NO:8) based on the published TNF sequence (Wang, et al., Science, Vol 228, pgs 149–154 (1985), (Genbank accession #M10988 incorporated herein by reference). Primers were designed to include BglII and XhoI restriction sites. The PCR product is cut with BglII and XhoI and cloned into BglII and XhoI digested pBg (FIG. 3 and as described in PCT Application No. W091/10728, published Jul. 25, 1991, incorporated herein by reference) to form pT2. (FIG. 4).

PCR reactions then are carried out using primers P1, P2, P3 and P4 in order to amplify the Adenovirus 5 fiber tail and shaft sequences as well as the mature TNF protein sequence from pGEM5F and pT2, respectively.

Figure 5:
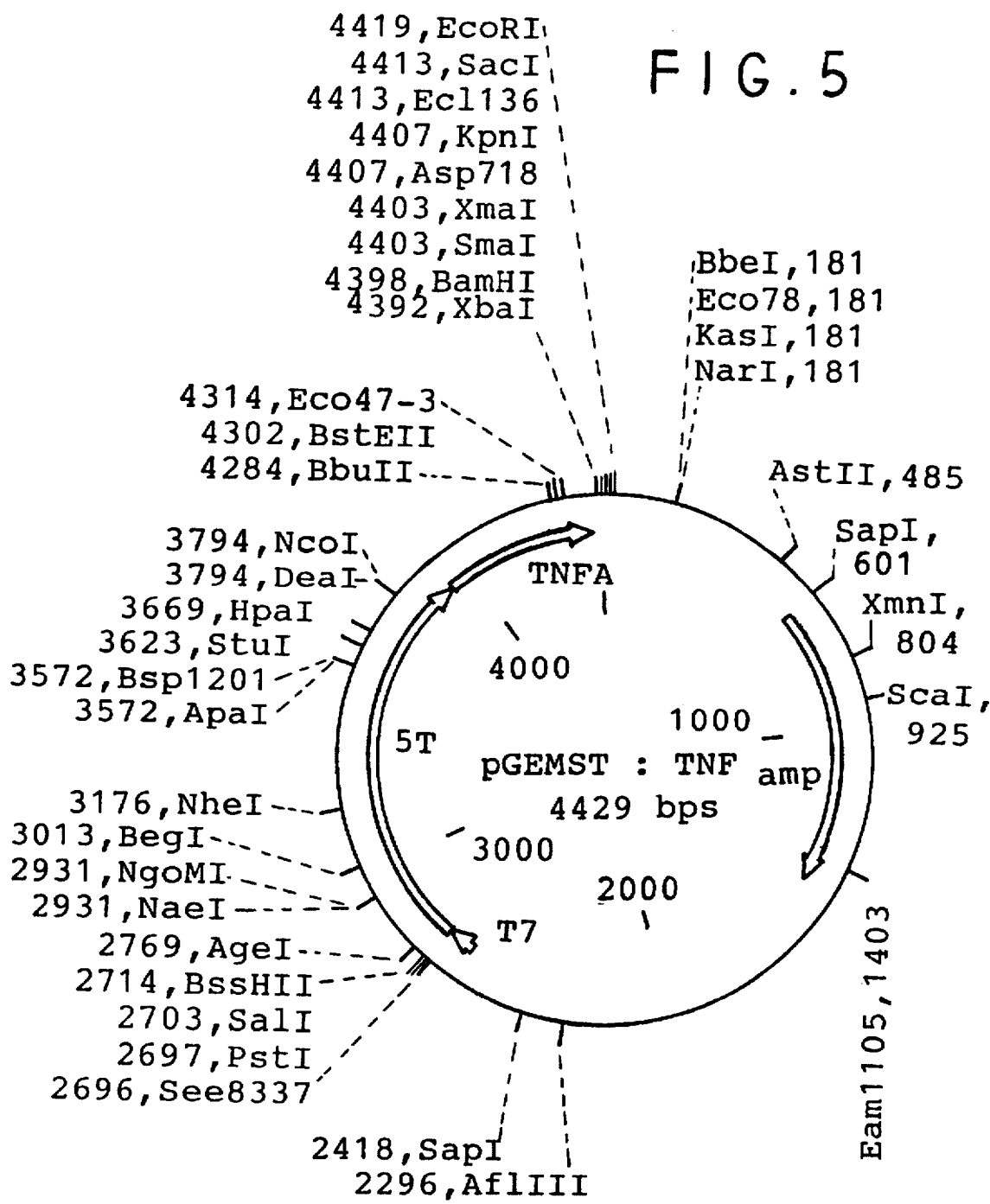
FIG. 5 is a map of the plasmid pGEM5F::TNF.

The PCR reactions are carried out as follows: 5 min -92° C., then 45 sec -92° C., 45 sec -52° C., 2 min -72° C. for 30 cycles and then 8 min -72° C. The PCR products then are analyzed on a 1% agarose tris/acetate/EDTA gel. The expected 1.2 Kb 5F tail and shaft and the 0.47 Kb TNF fragments are excised from the gel and the second PCR reaction is carried out as described using the primers P1 and P4 to amplify the 1.67 Kb full length Adenovirus 5 fiber: TNF chimera. The nucleotide sequence of the cloned insert is determined by DNA sequencing and a clone having a perfect match with the expected sequence can be selected. The insert is cut with SalI and XbaI and cloned into SalI and XbaI digested pGEM4Z to form pGEM5F:TNF (FIG. 5).

B. In vitro expression and analysis of the 5F:TNF chimera

Expression and function of the Adenovirus 5 fiber:TNF chimera is analyzed in an in vitro transcription/translation cell binding experiment using an adaptation of the surface receptor binding assay described by Leone, et al. (1992) Cell. 71:479–488, incorporated herein by reference. A 1 μg aliquot of the pGEM5F:TNF DNA is used in the in vitro transcription/translation reaction (Promega) using [$^{35}$—S] L-methionine. Protein sample preparation for SDS PAGE analysis is carried out such that the trimeric state of the 5F:TNF chimera will remain intact (Novelli et al., (1991) J. Biol. Chem. 266: 9299–9303 incorporated herein by reference.). The translated protein products are analyzed by nondenaturing 4/15% SDS PAGE and fluorography. The expected molecular weights for the 5F:TNF monomer and trimer are approximately 55 kDa and 165 kDa, respectively. Western analysis of the translated protein products demonstrates the correct trimer conformation by reactivity with monoclonal antibodies either specific to Adenovirus 5 fiber trimer, 2A6.36, or to the TNF trimer (Endogen, Inc.). The function of the 5F:TNF trimer then is demonstrated by interaction with the TNF cell surface receptors. A variety of different cell types which express the TNF receptor can be used in this assay such as: HL60 monocyte/macrophages and U937 monocyte/macrophages. Approximately $1 \times 10^6$ cells are plated onto 60 mm tissue culture dishes and are allowed to attach overnight at 37° C. in a 5% $CO_2$ atmosphere. The labeled protein mixture from the in vitro transcription/translation is applied to the cell surface monolayer and allowed to incubate for one hour at room temperature. The cell surface is washed extensively and the cells are lyzed to analyze cell-associated labeled protein. Samples will be prepared for nondenaturing 4/15% SDS PAGE and fluorography. If the 5F:TNF chimera is functional, the 165 kDa trimer should interact with the TNF receptor.

Specificity of receptor binding is demonstrated through competition analysis using purified human TNF (Endogen, Inc.) and antibodies specific to TNF (Endogen, Inc.) as competitors. A functional 5F:TNF protein which interacts with the TNF receptor will not bind in the presence of excess competitor.

C. Incorporation of 5F:TNF Chimera into Adenovirus

The modified fiber can be incorporated into an intact adenovirus by one of two methods. Both methods utilize a fiber-deleted Adenovirus 5 which is constructed as described in Falgout, et al., J. Virol., Vol. 61, pgs. 3759–3768 (1987), incorporated herein by reference.

In one method, a shuttle vector, pAVS6 (FIG. 9), first is constructed.

Figure 6:
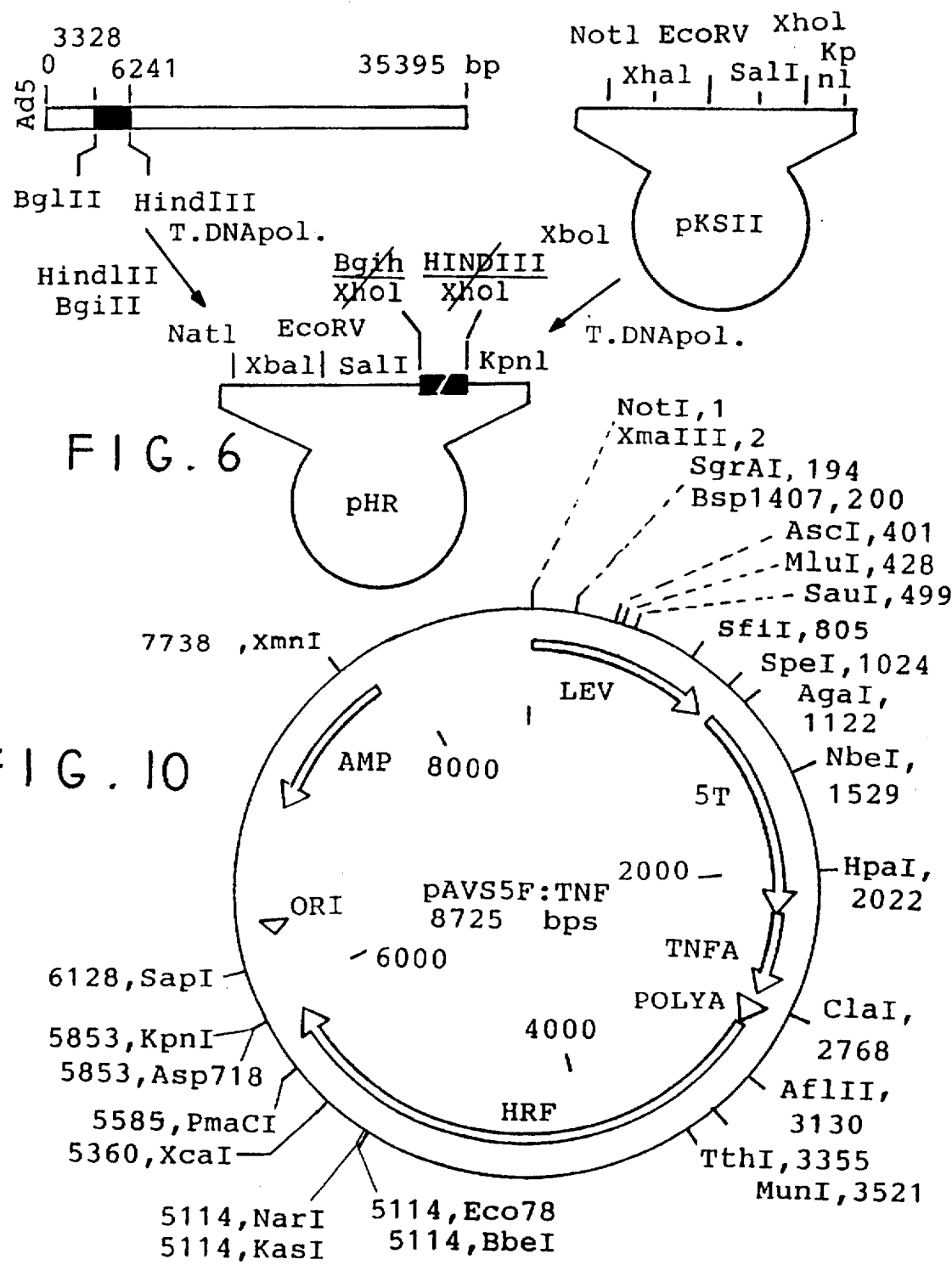
FIG. 6 is a schematic of the construction of the plasmid pHR.

The adenoviral construction shuttle plasmid pAVS6 was constructed in several steps using standard cloning techniques including polymerase chain reaction based cloning techniques. First, the 2913 bp Bgl II, HindIII fragment was removed from Ad-d1327 and inserted as a blunt fragment into the XhoI site of PBluescript II KS (Stratagene, La Jolla, Calif.) (FIG. 6). Ad-d1327 (Thimmappaya, et al., Cell, Vol. 31, pg. 543 (1983), incorporated herein by reference) is identical to Adenovirus 5 except that an XbaI fragment including bases 28591 to 30474 (or map units 78.5 to 84.7) of the Adenovirus 5 genome, and which is located in the E3 region, has been deleted. The complete Adenovirus 5 genome is registered as Genbank accession #M73260, incorporated herein by reference, and the virus is available from the American Type Culture Collection, Rockville, Md. U.S.A. under accession number VR-5.

Ad-d1327 was constructed by routine methods from Adenovirus 5 (Ad5). The method is outlined briefly as follows and previously described by Jones and Shenk. Cell 13:181–188, (1978). Ad5 DNA is isolated by proteolytic digestion of the virion and partially cleaved with XbaI restriction endonuclease. The XbaI fragments are then reassembled by ligation as a mixture of fragments. This results in some ligated genomes with a sequence similar to Ad5, except excluding sequences 28591 bp to 30474 bp. This DNA is then transfected into suitable cells (e.g. KB cells, HeLa cells, 293 cells) and overlaid with soft agar to allow plaque formation. Individual plaques are then isolated, amplified, and screened for the absence of the 1878 bp E3 region XbaI fragment.

The orientation of this fragment was such that the BglII site was nearest the T7 RNA polymerase site of pKSII and the HindIII site was nearest the T3 RNA polymerase site of PBluescript II KS. This plasmid was designated pHR. (FIG. 6).

Second, the ITR, encapsidation signal, Rous Sarcoma Virus promoter, the adenoviral tripartite leader (TPL) sequence and linking sequences were assembled as a block using PCR amplification (FIG. 7). The ITR and encapsidation signal (sequences 1–392 of Ad-d1327 [identical to sequences from Ad5, Genbank accession #M73260], incorporated herein by reference) were amplified (amplification 1) together from Ad-d1327 using primers containing NotI or AscI restriction sites. The Rous Sarcoma Virus LTR promoter was amplified (amplification 2) from the plasmid pRC/RSV (sequences 209 to 605; Invitrogen, San Diego, CA) using primers containing an AscI site and an SfiI site. DNA products from amplifications 1 and 2 were joined using the "overlap" PCR method (amplification 3) (Horton, et al., *Biotechniques*, Vol. 8, pgs. 528–535 (1990)) with only the NotI primer and the SfiI primer. Complementarity between the AscI containing end of each initial DNA amplification product from reactions 1 and 2 allowed joining of these two pieces during amplification. Next the TPL was amplified (amplification 4) (sequences 6049 to 9730 of Ad-d1327 [identical to similar sequences from Ad5, Genbank accession #M73260]) from cDNA made from mRNA isolated from 293 cells (ATCC accession No. CRL 1573) infected for 16 hrs. with Ad-d1327 using primers containing SfiI and XbaI sites respectively. DNA fragments from amplification reactions 3 and 4 were then joined using PCR (amplification 5) with the NotI and XbaI primers, thus creating the complete gene block.

Third, the ITR-encapsidation signal-TPL fragment was then purified, cleaved with NotI and XbaI and inserted into the NotI, XbaI cleaved pHR plasmid. This plasmid was designated pAvS6A and the orientation was such that the NotI site of the fragment was next to the T7 RNA polymerase site (FIG. 8).

Figure 8:
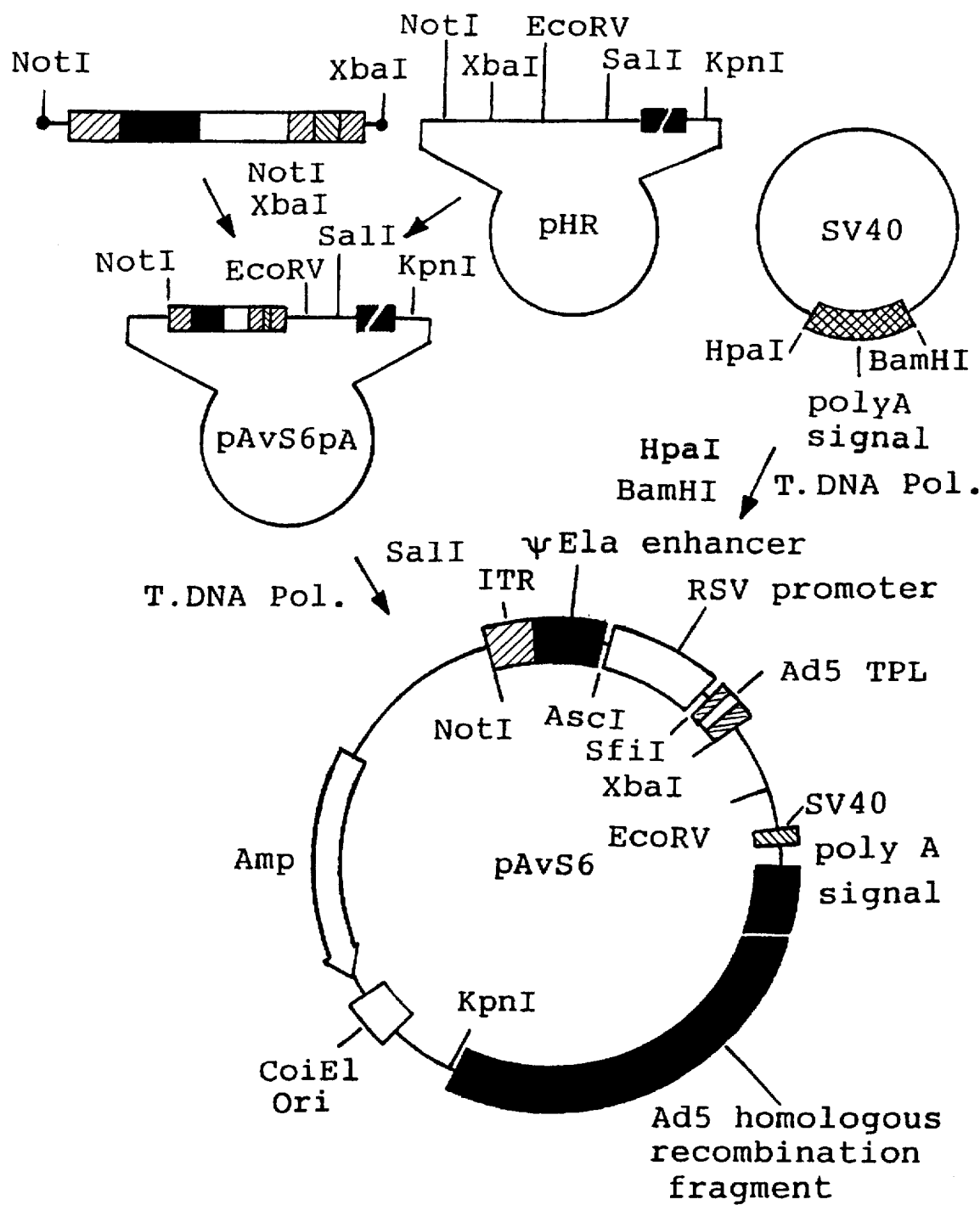
FIG. 8 is a schematic of the construction of plasmid pAVS6.
Figure 9:
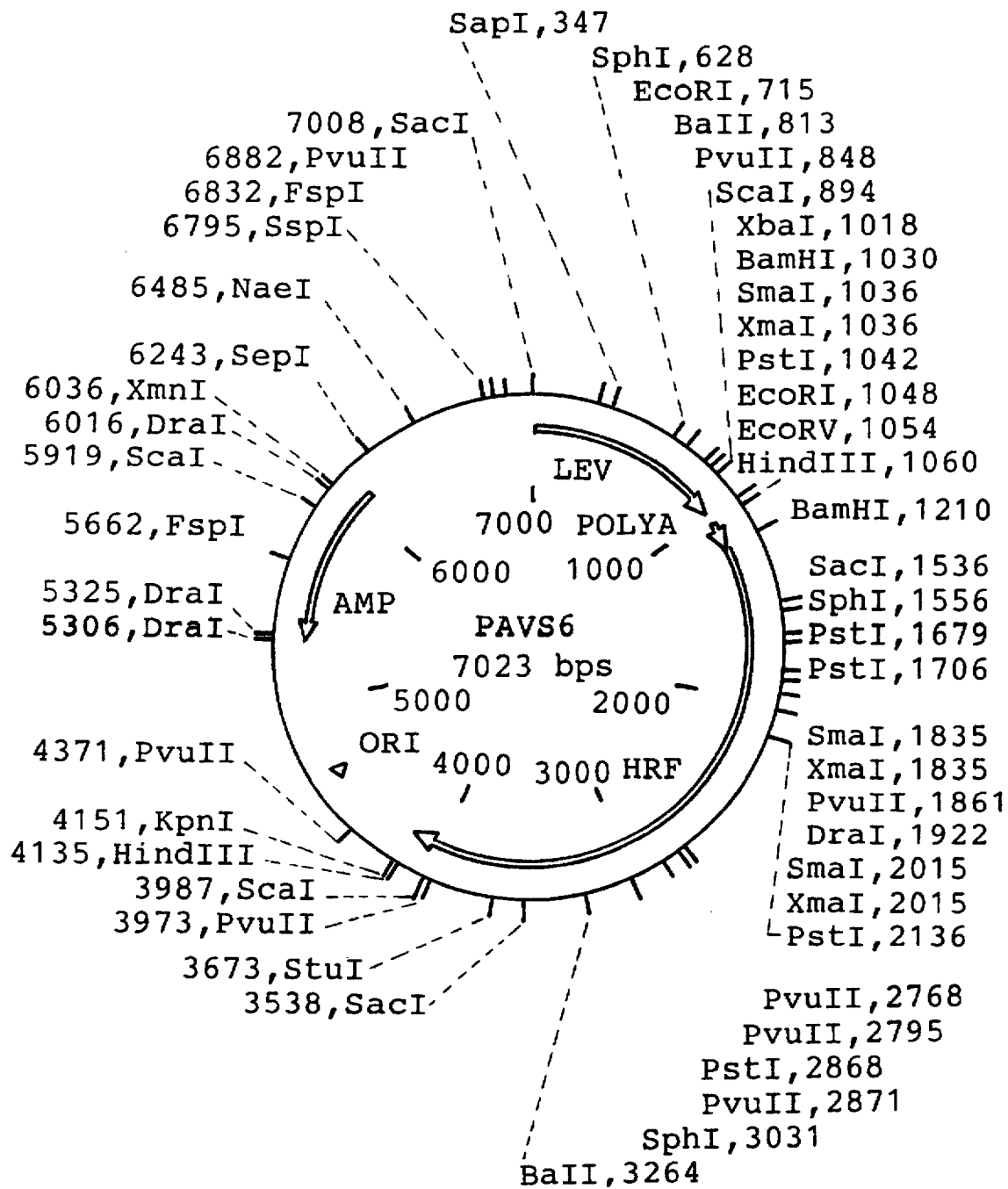
FIG. 9 is a map of plasmid pAVS6.

Fourth, the SV40 early polyA signal was removed from SV40 DNA as an HpaI-BamHI fragment, treated with T4 DNA polymerase and inserted into the SalI site of the plasmid pAvS6A-(FIG. 8) to create pAvS6 (FIGS. 8 and 9).

The 5F:TNF chimeric construct then is cloned into pAVS6. The plasmid pGEM5F::TNF is digested with SmaI and SalI to obtain the 5F:TNF fragment. The ends of the fragment are filled in with Klenow DNA polymerase to create a blunt ended 5F:TNF fragment. The blunt ended 5F:TNF fragment then is cloned into EcoRV digested pAVS6 to form pAVS5F::TNF (FIG. 10). pAVS5F::TNF and ClaI digested Ad 5 dl 1021, which is an adenoviral vector wherein DNA encoding the Adenovirus 5 fiber is deleted (Falgout, et al. 1987), are co-transfected into 293 cells using calcium phosphate precipitation. Homologous recombination produces a recombinant adenoviral vector particle containing the 5F:TNF gene.

Figure 12:
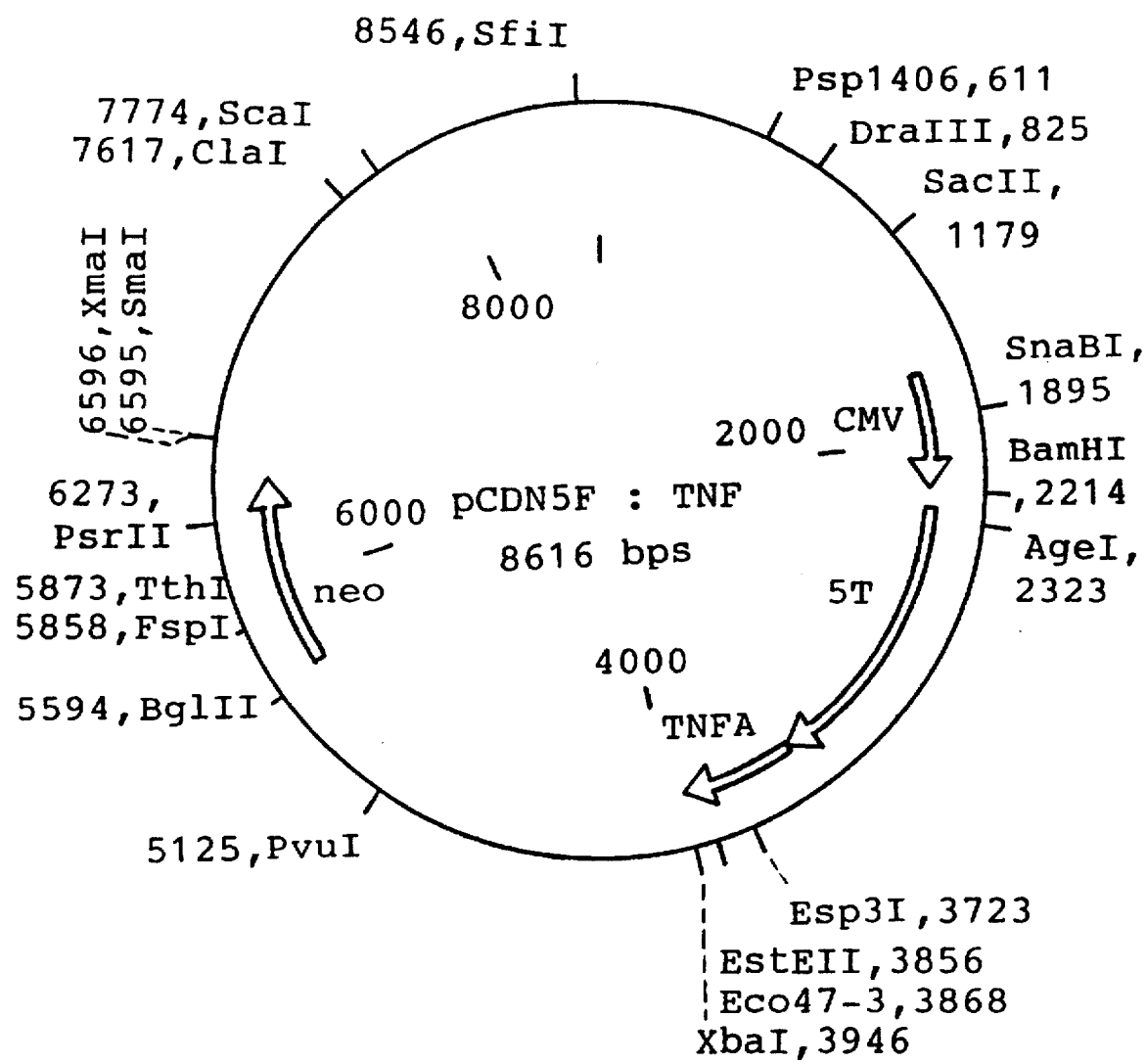
FIG. 12 is a map of plasmid pCDN5F::TNF.

In the second method, pGEM5:: TNF is digested with SalI, and the ends of the linearized vector are treated with Klenow DNA polymerase to create blunt ends. The blunt ended, linearized pGEM5F::TNF is digested further with XbaI and cloned into EcoRV and XbaI digested pcDNA-neo (Invitrogen, FIG. 11) to form pcDN5F::TNF. (FIG. 12). pcDN5F::TNF and Ad 5 dl 1021 DNA (Falgout, et al., 1987) are co-transfected into 293 cells using calcium phosphate precipitation to produce a recombinant adenoviral vector particle containing the 5F:TNF fiber protein.

The function of the recombinant 5F:TNF adenovirus is assessed by infection and cell receptor binding assays. To assess virus:TNF receptor interaction and infectivity, plaque assays, cellular receptor binding or competition assays are carried out using the purified virus as the receptor ligand and purified TNF or anti-TNF antibodies as competitors. An infectious recombinant adenovirus expressing 5F:TNF protein which interacts with the TNF receptor will not infect cells in the presence of excess competitor.

For in vitro transduction of cells, an aliquot of the infectious viral particles containing up to about $10^{14}$ plaque forming units, is added to cells expressing a TNF receptor, such as for example, HL60 monocyte/macrophages and U937 monocyte/macrophages, and the viral particles are allowed to bind. For in vivo transduction of cells, an aliquot of the infectious viral particles of up to about $10^{14}$ plaque forming units is administered by intravenous infusion, whereby such infectious viral particles will infect cells expressing a TNF receptor.

Example 2

Construction of Adenovirus 5

Including a Chimeric Fiber of

Adenovirus 5 Fiber Protein and ApoE

A. Construction of Vector Including DNA Encoding the Adenovirus 5 Fiber:apoE Chimera The Adenovirus 5 fiber:apoE (5F:apoE) chimera is prepared by PCR gene overlap extension (Horton et al., (1990) *Biotechniques* 8:528–535). The Adenovirus 5 fiber tail, shaft, and head regions, amino acids 1 to 581, are connected with a tandem repeat of the apoE-LDL receptor binding domain, amino acids 141 to 155. The DNA encoding ApoE is registered as Genbank accession nos. K00396 and X00199. This tandem repeat has been shown to interact efficiently with the LDL receptor (Dyer and Curtiss (1991) *J. Biol. Chem.* 266:22803–22806, incorporated herein by reference). The 5F:apoE chimera can be modified further by substitution or deletion of selected amino acid residues in the head region of the adenovirus 5 fiber protein such that the interaction with the normal adenovirus 5 cellular receptor is abolished using methods as described in McClelland, et al., *Proc. Nat. Acad. Sci.*, Vol. 88, pgs. 7993–7997 (1991), incorporated herein by reference. The primers which are used in the PCR construction are as follows:

5F: P1 5'-ATGGAGATCTTACTGAAGGCACAGC CTATA-3' (SEQ ID NO:9)

ApoE: P2 5'-CCGCTTACGCAGCTTGCGCAGT TCTTGGGCAATGTATGAAAA-3' (SEQ ID NO:10)

P3 5'-GTCATCGGCATCGCGGAGGAGCCGCTTA CGCAGCTTGCGCAG-3' (SEQ ID NO:11)

P4 5'-CTTACGCAGCTTGCGCAGCAGGTCATCG GCATCGCGGAGGAG-3' (SEQ ID NO:12)

P5 5'-ATCTTCATCGCGGAGGAGCCGCTTACGC AGCTTGCGCAGCAG-3' (SEQ ID NO:13)

P6 5'-TTAATGGAATCCTTACAGGTCATCGGCAT CGCGGAGGAGCCCG-3' (SEQ ID NO:14)

Figure 13:
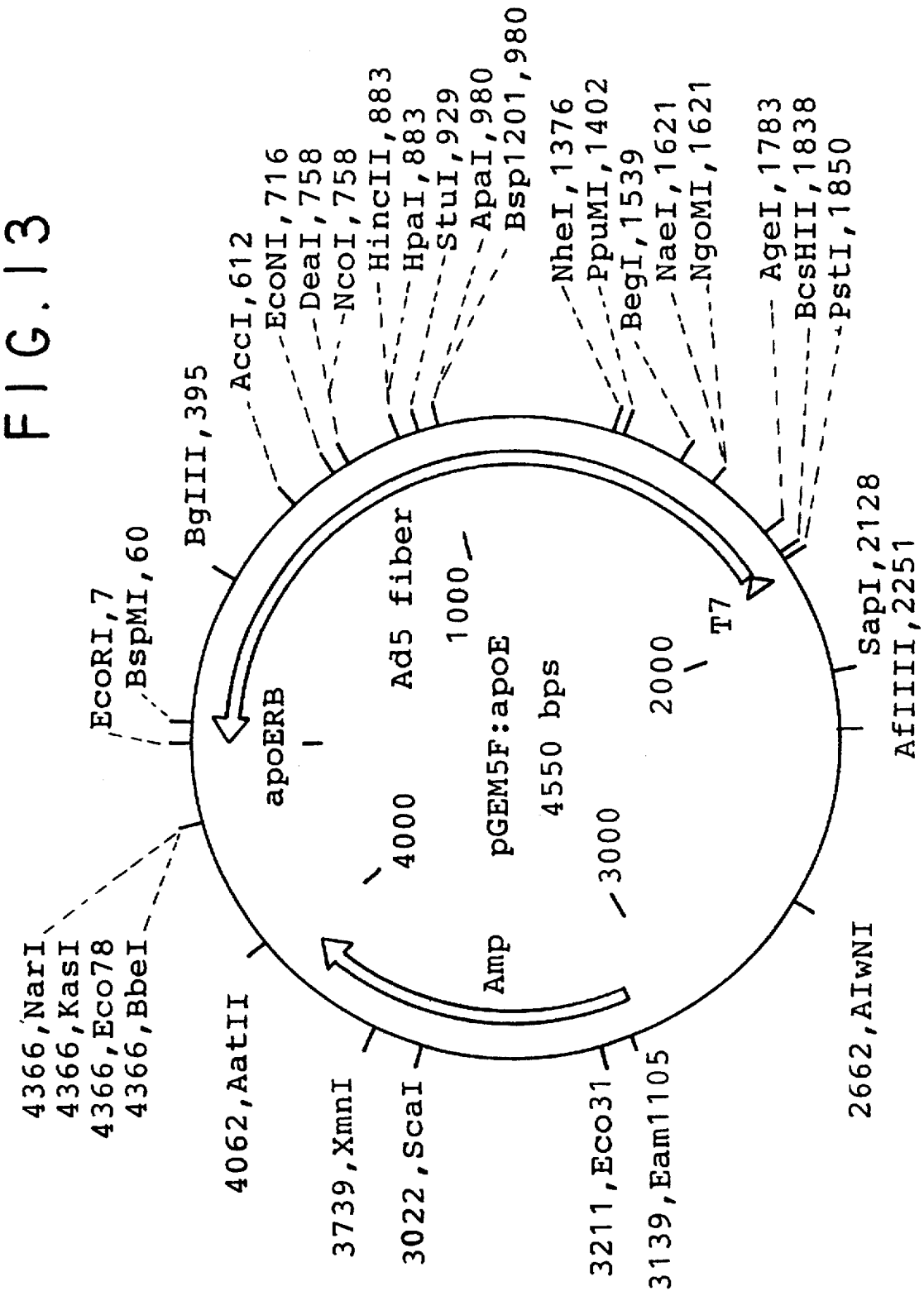
FIG. 13 is a map of plasmid pGEM5F::apoE.

The primers P1 and P2 are designed to amplify a portion of the Adenovirus 5 fiber gene, nucleotides 1920 to 2221, Genebank #M18369. The primers P1 and P6 are designed to include Bgl II and Eco RI restriction enzyme sites, respectively, for cloning into the expression vector, pGEM5F. (FIG. 2) The template which is used for amplifying the appropriate sequences is pGEM5F which contains the correct cDNA for the Adenovirus 5 fiber gene. The PCR reactions are carried out as follows: 5 min −92° C., then 45 sec −92° C., 45 sec −55° C., 2 min −72° C. for 30 cycles and then 8 min −72° C. The PCR products then are analyzed on a 1% agarose tris/acetate/EDTA gel. The expected 0.322 Kb 5F:apoE fragment can be excised from the gel and the second PCR reaction is carried out as described using primers P1 and P3 to add on the appropriate apoE sequences onto the Adenovirus 5 fiber. A total of five PCR reactions are carried out using primer P1 with each of primers P2, P3, P4, P5, and P6 in succession to generate a tandem repeat of the apoE-LDL receptor binding domain. The PCR generated 5F:apoE fragment then is cloned into the full length Adenovirus 5 fiber construct, pGEM5F, using the Bgl II and Eco RI restriction enzyme sites to form pGEM5F::apoE. (FIG. 13). The nucleotide sequence of the cloned insert then is determined by DNA sequencing and a clone having a perfect match with the expected sequence can be selected.

B. In vitro expression and analysis of the 5F:apoE chimera

Expression and function of the 5F:apoE chimera is analyzed in an in vitro transcription/translation cell binding experiment using an adaptation of the surface receptor binding assay described by Leone et al. (1992) *Cell.* 71:479–488. A 1 µg aliquot of the pGEM5F:apoE DNA is used in the in vitro transcription/translation reaction (Promega) using [$^{35}$—S] L-methionie. Protein sample preparation for SDS PAGE analysis is carried out such that the trimeric state of the 5F:apoE chemera will remain intact (Novelli et al., (1991) *J. Biol. Chem.* 266: 9299–9303). The translated protein products are analyzed by nondenaturing 4/15% SDS PAGE and fluorography. The expected molecular weights for 5F:apoE monomer and trimer are 63 kDa and 189 kDa, respectively. Correct trimer conformation can be assessed by reactivity with monoclonal antibodies either specific to Adenovirus 5 fiber trimer, 2A6:36 and 4D2-5, or to the apoE-LDL receptor binding domain. The function of the 5F:apoE trimer then is assessed by interaction with cell surface LDL receptors. The cell surface binding assays are carried out using LDL receptor positive and negative cell lines such as CHO and CHO1d1A7 cells, respectively (Herz and Gerard (1993) *PNAS USA.* 90:2812–2816), incoporated herein by reference. Normal human fibroblasts and other cell lines which express the LDL receptor may also be used in this assay. Approximately 1×10$^6$ cells will be plated onto 60 mm tissue culture dishes and are allowed to attach overnight at 37° C. in a 5% CO$_2$ atmosphere. The labeled protein mixture from the in vitro transcription/translation is applied to the cell surface monolayer and is allowed to incubate for one hour at room temperature. The cell surface is washed extensively and the cells are lyzed to analyze cell associated labeled protein. Samples are prepared for nondenaturing 4/15% SDS PAGE and fluorography. A functional 5F:apoE chimeric protein trimer will interact with CHO cells but not with CHO1d1A7 cells.

Specificity of receptor binding is demonstrated through competition analysis using human LDL, purified human apoE, and anti-apoE or anti-LDL receptor antibodies as competitors. In the presence of excess competitor the 5F:apoE trimer will not interact with the surface LDL receptors on CHO cells.

C. Incorporation of 5F:apoE Chimera into Adenovirus

The modified 5F:apoE fiber then is incorporated into adenovirus.

Figure 14:
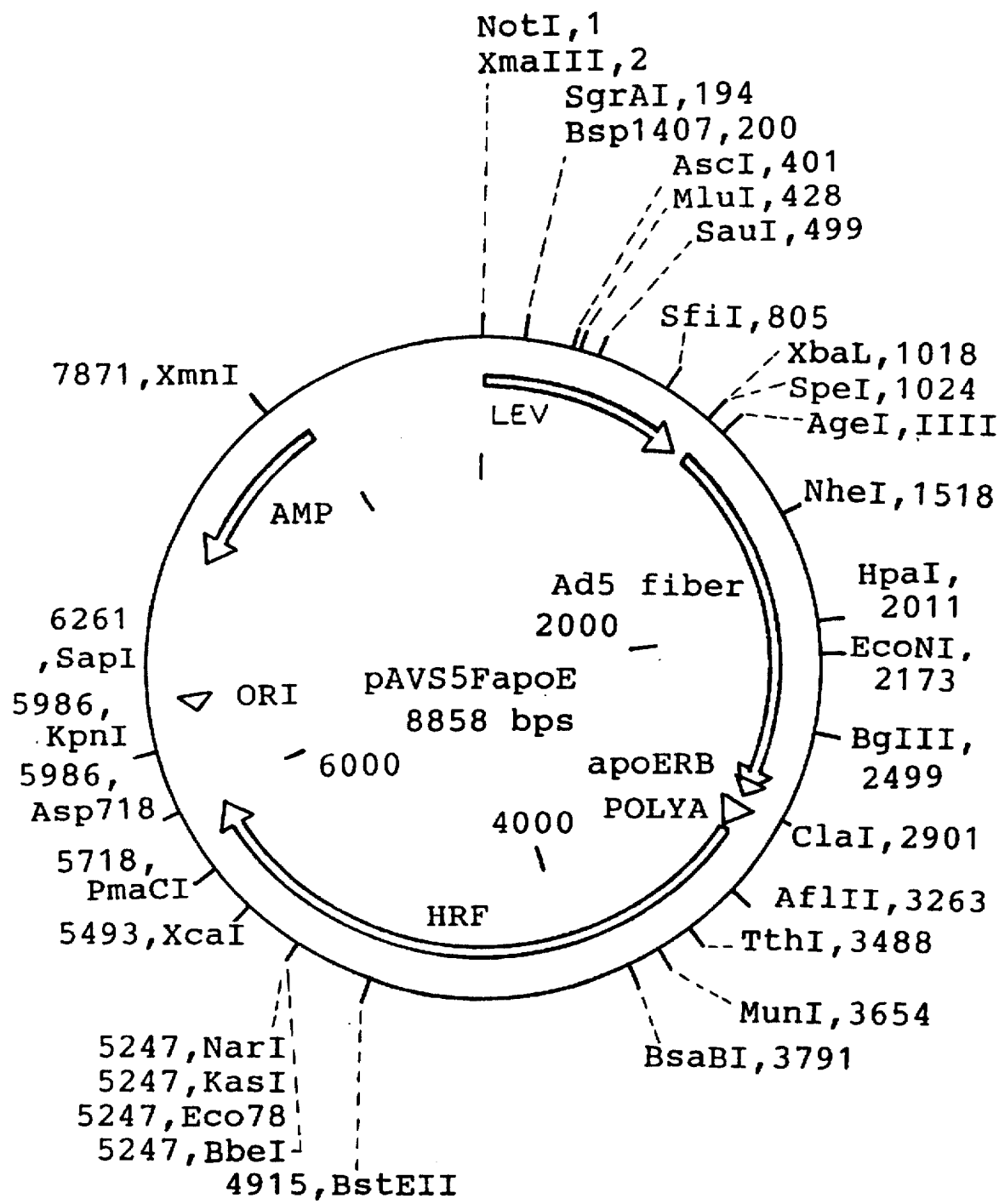
FIG. 14 is a map of plasmid pAVS5F::apoE.

The 5F:apoE chimeric construct is cloned into the shuttle vector pAVS6 (FIG. 9). pGEM5F::apoE is digested with EcoRI and BssHII to isolate the 5F:apoE fragment. The ends of the fragment are filled in with Klenow DNA polymerase to form a blunt ended 5F:apoE fragment. The blunt ended 5F:apoE fragment is then cloned into EcoRV digested pAVS6 to form pAVS5F::apoE. (FIG. 14.) pAVS5F::apoE and Cla I digested Ad 5 dl 1021 (Falgout, et al., 1987) are co-transfected into 293 cells using calcium phosphate precipitation. Homologous recombination produces a recombinant adenoviral vector particle containing the 5F:apoE gene.

The function of the recombinant 5F:apoE adenovirus is assessed by infection and cell receptor binding assays. To assess virus:LDL receptor interaction and infectivity, plaque assays, cellular receptor binding, and/or competition assays are carried out using the purified adenovirus as the receptor ligand and purified apoE or anti-LDL receptor antibodies as competitors. An infectious recombinant adenovirus expressing 5F:apoE protein which interacts with the LDL receptor will not infect cells in the presence of excess competitor.

For in vitro transduction of cells, an aliquot of the infectious viral particles containing up to about 10$^{14}$ plaque forming units is added to cells expressing the LDL receptor, such as, for example, liver cells, and the viral particles are allowed to bind to the cells. For in vivo transduction of cells, an aliquot of the infectious viral particles containing up to about 10$^{14}$ plaque forming units, is administered by intravenous infusion, whereby such infectious viral particles will infect cells expressing the LDL receptor, such as liver cells, for example.

Example 3

Construction of Adenovirus 5

Figure 15:
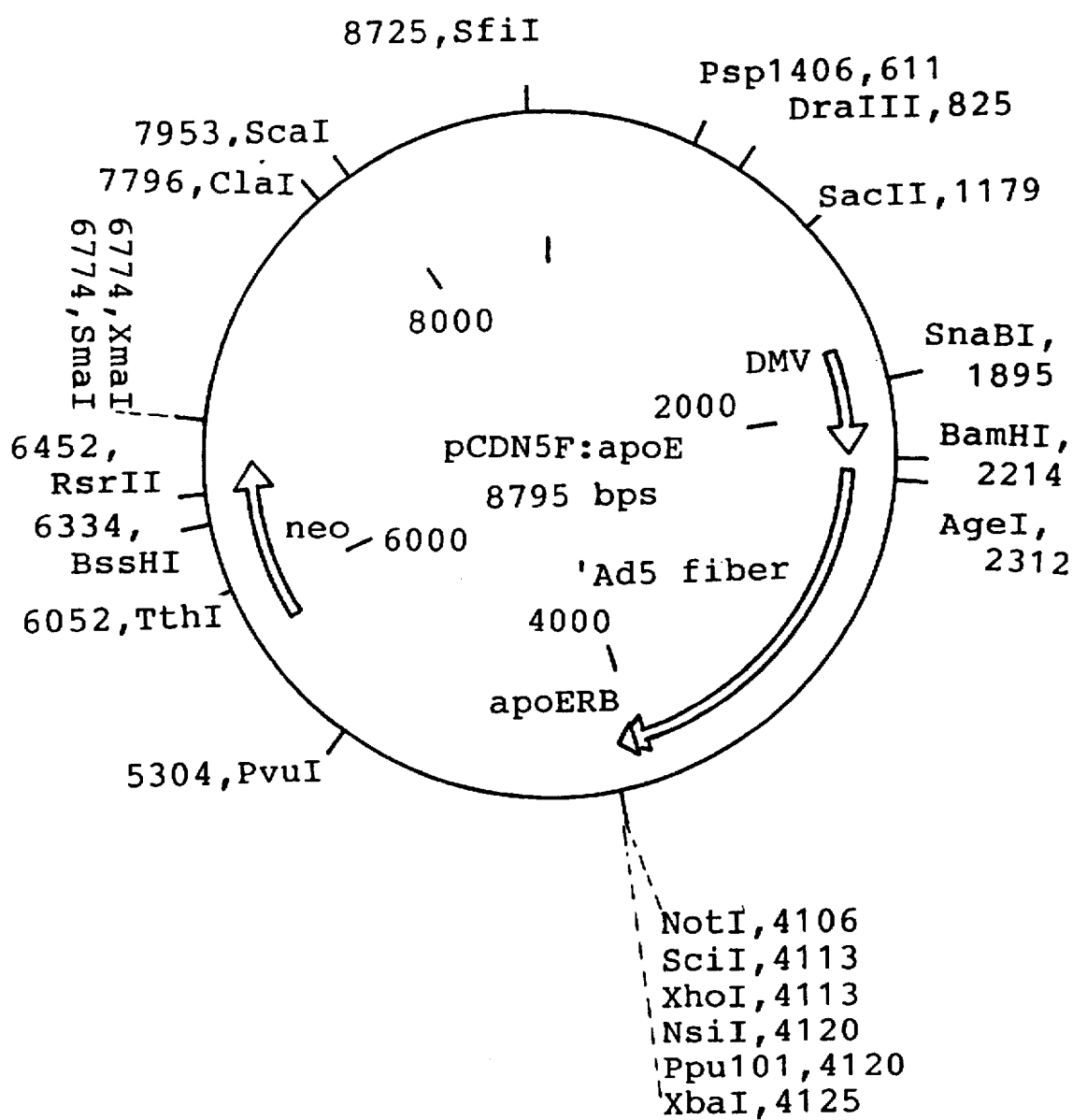
FIG. 15 is a map of plasmid pCDN5F::apoE.

Including a Chimeric Fiber of Adenovirus 5 Fiber Protein and ApoE, and a Factor IX Gene A. Construction of pCDN5F:apoE pGEM5F:apoE is digested with EcoRI and BssHII to isolate the 5F:apoE fragment. The ends of the 5F:apoE fragment are treated with Klenow DNA polymerase to create blunt ends. The blunt ended 5F:apoE fragment is cloned into EcoRV digested pcDNA-neo to created pCDN5F:apoE. (FIG. 15).

Figure 16:
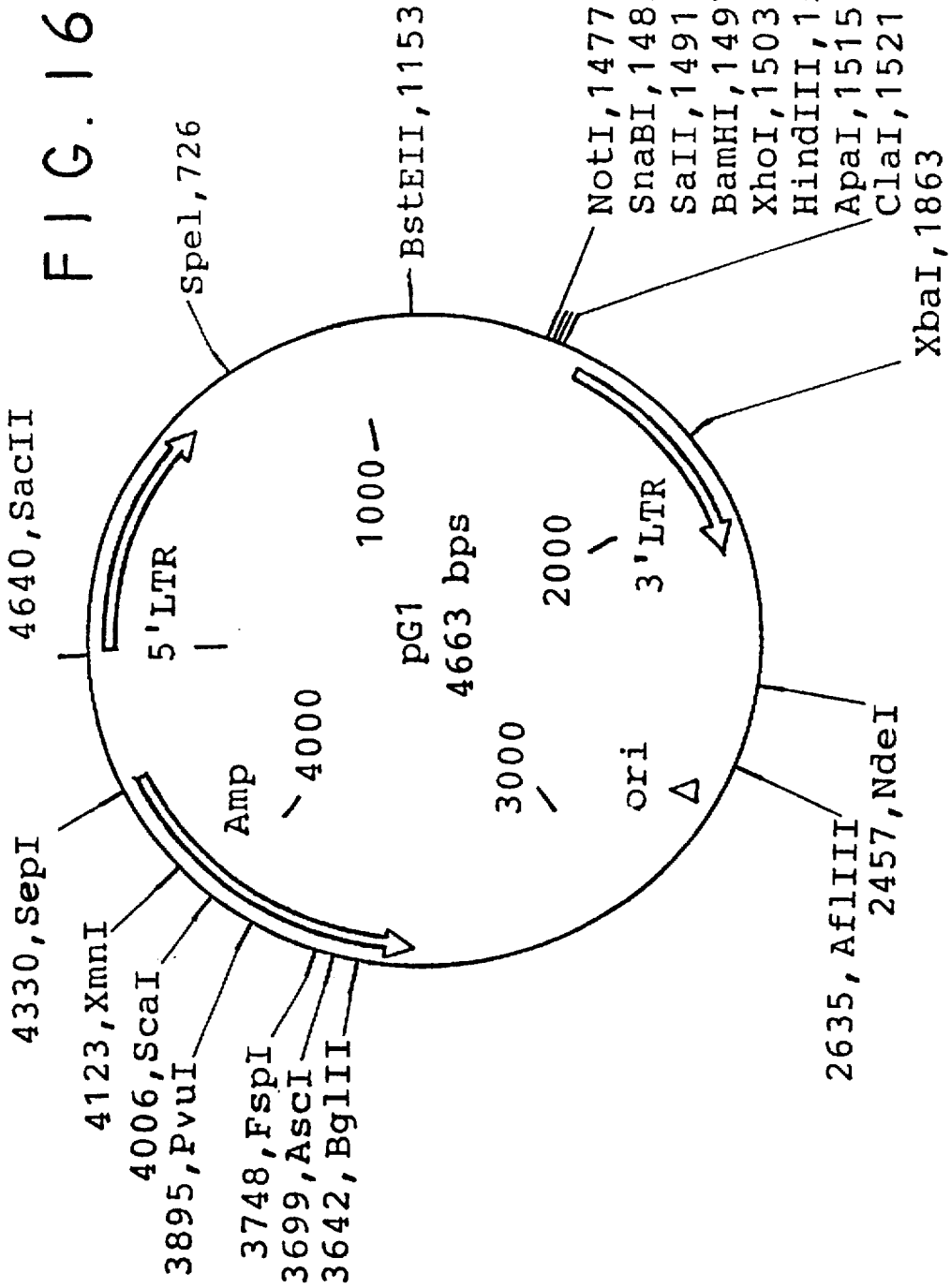
FIG. 16 is a map of plasmid pG1.
Figure 17:
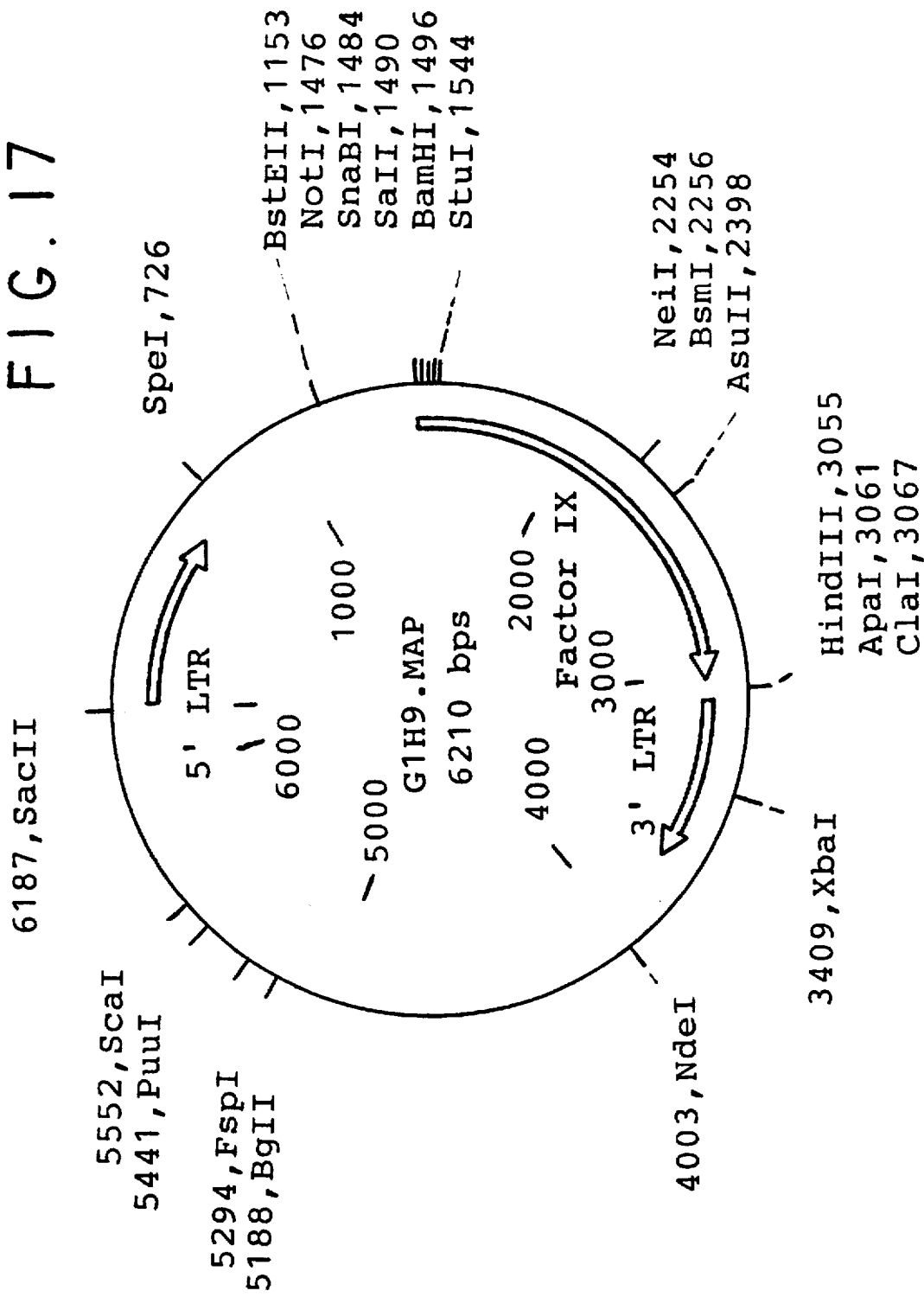
FIG. 17 is a map of plasmid pG1H9.

B. Construction of pG1H9 pG1 (described in PCT Application No. WO91/10728 published Jul. 25, 1991) (FIG. 16) is cut with BamHI and HindIII. pL1XSN (Palmer, et al, *Blood,* Vol. 73, No. 2, pgs. 438–445 (Feb. 1989), incorporated herein by reference), which contains a Factor IX gene, an SV40 promoter, and a neo$^R$gene, is also cut with BamHI and HindIII. The resulting BamHI-HindIII fragment, which contains the Factor IX gene, is then ligated to the BamHI-HindIII digested pG1 to form pG1H9. (FIG. 17).

Figure 18:
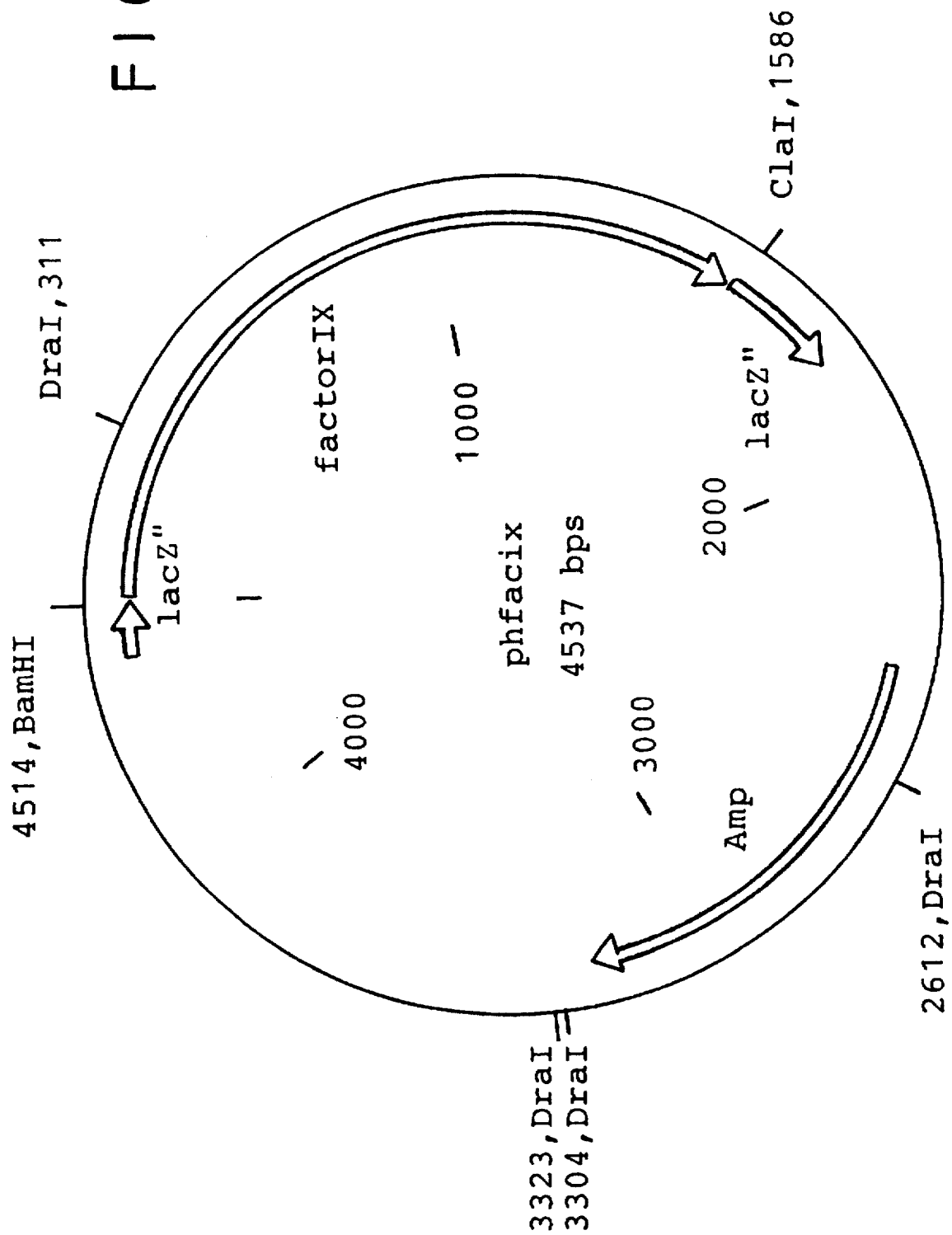
FIG. 18 is a map of plasmid phfacIX.
Figure 19:
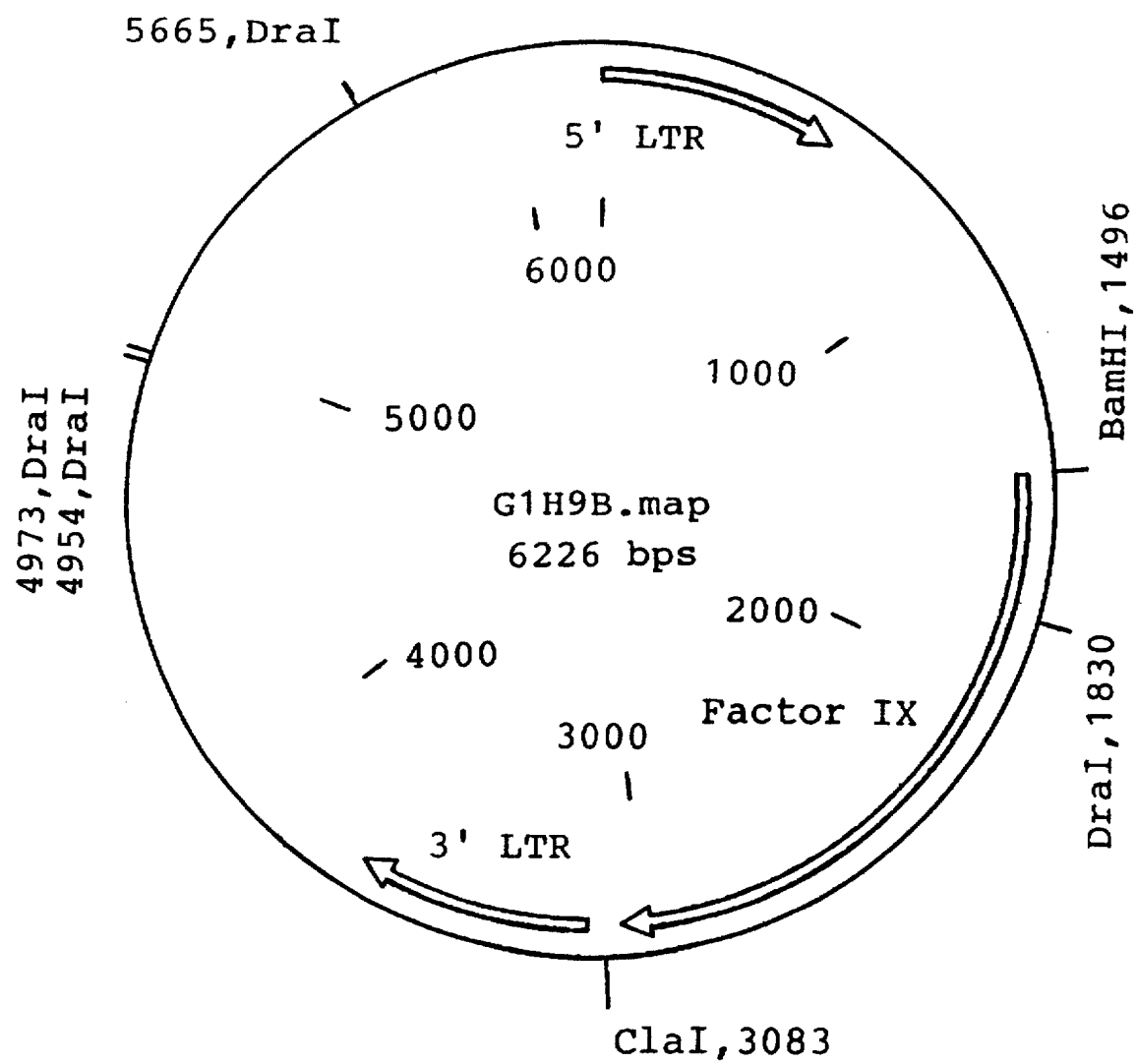
FIG. 19 is a map of plasmid pG1H9B.

C. Construction of pG1H9B pG1H9B (FIG. 19) was constructed so that the 5' untranslated region of the human Factor IX cDNA is identical to the natural 5' untranslated region. Such is not the case for pG1H9 because of an inversion in the DNA sequence.

pG1H9B was constructed as follows. First, a cDNA clone of human Factor IX was generated by PCR amplification of human liver cDNA followed by subcloning into the plasmid pBluescript SK-(Stratagene). The resulting plasmid was designated phfacIX (FIG. 18). phfacIX then was cut with BamHI and DraI, and the 334 bp fragment corresponding to the 5' end of the Factor IX cDNA was isolated. pG1H9 was cut with DraI and ClaI and the 1253 bp fragment encoding the 3' end of the Factor IX cDNA was isolated. The two isolated DNA fragments encoding Factor IX cDNA were ligated into the pG1H9 backbone which had been cut with BamHI and ClaI to generate pG1H9B (FIG. 19).

D. Construction of AVS6H9B

Factor IX cDNA (FIG. 20), which contains the entire protein coding sequence, 26 base pairs of 5' untranslated DNA (assuming translation starts at the third ATG of the message) and 160 base pairs of 3' untranslated DNA, was excised from pG1H9B by restriction digestion with ClaI, followed by filling in the 5' overhang using Klenow, followed by restriction digestion with SmaI.

Figure 21:
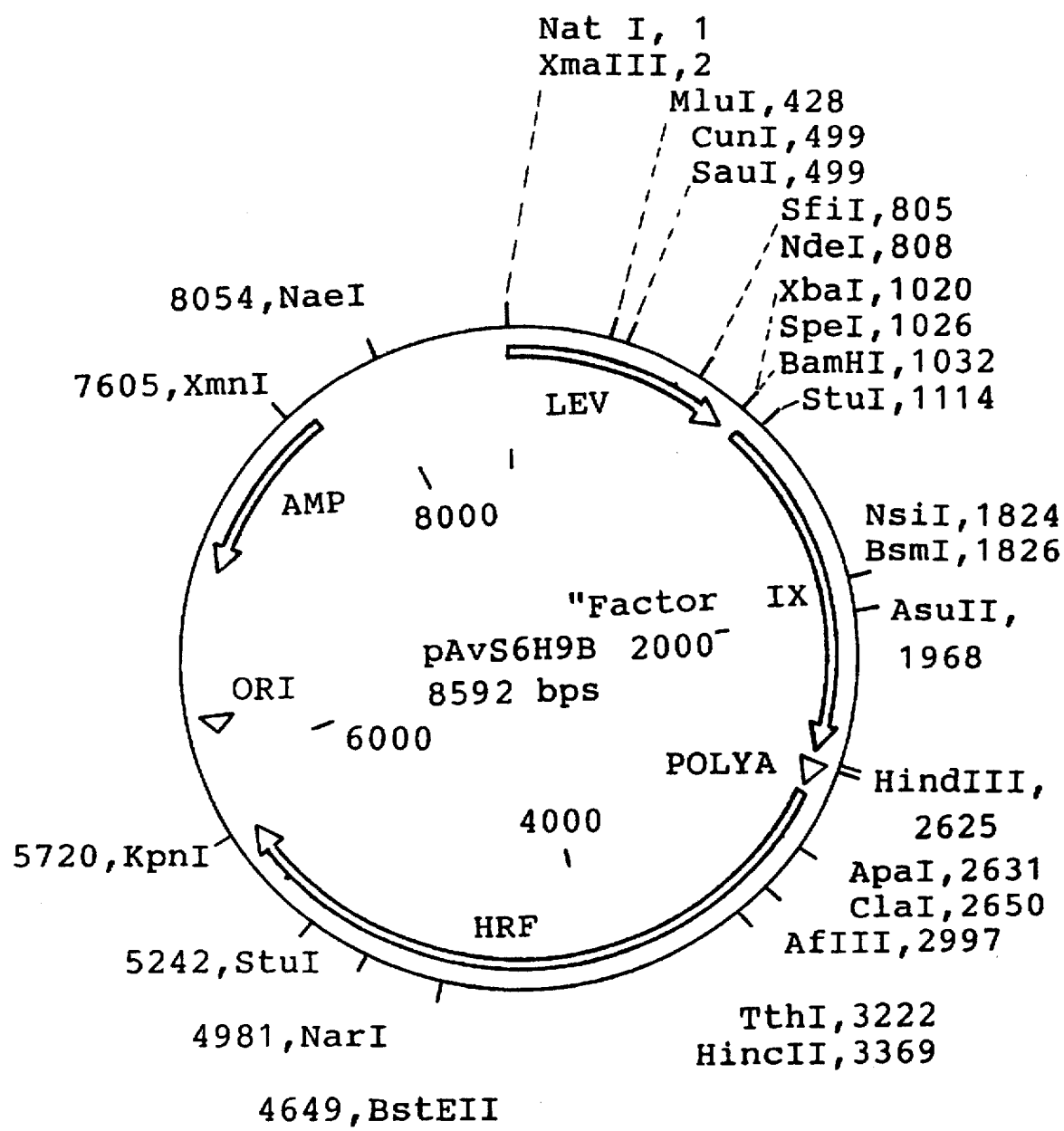
FIG. 21 is a map of plasmid pAVS6H9B.

The fragment encoding Factor IX was isolated by electrophoresis in a 1.0% agarose gel followed by electroelution of the DNA. This fragment was subcloned into pAVS6 which had been linearized with EcoRV and treated with calf intestinal phosphatase. The resulting shuttle plasmid pAvS6H9B (FIG. 21), contains the 5' inverted terminal repeat of adenovirus type 5 (Ad 5), the origin of replication of Ad 5, the Ad 5 encapsidation signal, the E1a enhancer, the RSV promoter, the tripartite leader sequence of Ad 5, Factor IX cDNA, the SV40 early polyadenylation signal, and Ad 5 sequences from nucleotide positions 3329–6246.

In order to generate a recombinant 5F:apoE adenovirus containing human Factor IX cDNA, 293 cells are transfected with pCDN5F::apoE, Cla I digested Ad 5 dl1021 DNA (Falgout, et al., 1987), and pAVS6H9B digested with NotI and KpnI. The transfection is carried out by calcium phosphate precipitation, and infectious viral particles are generated which incorporate the 5F:apoE chimeric protein, and a gene encoding human Factor IX.

For in vitro transduction of cells, an aliquot of the infectious viral particles containing up to about $10^{14}$ plaque forming units is added to cells expressing the LDL receptor, such as, for example, liver cells, and the viral particles are allowed to bind to the cells. Upon transfection, the cells express Factor IX in vitro. For in vivo transduction of cells, an aliquot of the infectious viral particles containing up to about $10^{14}$ plaque forming units, is administered by intravenous infusion, such as, for example, by pottal vein infusion, whereby such infectious viral particles will infect cells expressing the LDL receptor, such as liver cells, for example. Once the liver cells are transfected with the invectious viral particles, the liver cells will express Factor IX in vivo.

Example 4

Construction of Adenoviruses Containing the CD30 Ligand

An approach for incorporation of modified fiber genes into the adenovirus genome using yeast artificial chromosomes (YAC) has been designed. The reagents necessary for this approach are described in Ketner, et al., Proc. Nat. Acad. Sci., Vol. 91, pgs. 6186–6190 (June 1994). A plasmid, p680.2 (FIG. 22) has been constructed which can be used to direct substitutions of modified fiber genes into the adenovirus YAC by a two step gene replacement method. This vector contains part of the 5F tail region and flanking upstream and downstream targeting sequences. Modified fiber sequences are designed to be inserted at the Hind III restriction site at residue 6549. The vector contains an origin or replication and an ampicillin resistance gene for plasmid maintenance in bacteria.

p680.2 is constructed from p680. (Spencer, et al., Methods, Vol. 5, pgs. 161–175 (1993)). p680 is an integrating plasmid which contains the leu 2 gene and the dominant cycloheximide-sensitivity allele (CHY2[3]) of CHY2. (Zaret, et al., J. Bacteriol., Vol. 162, pgs. 579–583 (1985)). The leu 2 gene serves as a positive selection for the integration step, and the CHY2[3] gene serves as a negative selection for sensitivity to cycloheximide in the excisional step of the two step gene replacement technique.

The construction of p680.2 involved two cloning steps. First, the target region 3' of the adenovirus 5 fiber gene was amplified by PCR as a 1 kb Xho I to Apa I fragment from the 2937 bp Hind III "F" fragment of adenovirus 5 genomic DNA. The sequence of the 43 base sense primer containing Xho I and Bam HI restriction sites used for the amplification of the 1 kb fragment is as follows:

5'-GGGCTCGAGGGATCCAGAATCGTTTGTGTTAT GTTTCAACGTG-3' (SEQ ID NO:15)

The sequence of the 37 base antisense primer containing an Apa I restriction site is as follows:

5'-CAAGGGCCCTGTGCCAACATTGATATCATGAC GAGCA-3' (SEQ ID NO:16)

Figure 22:
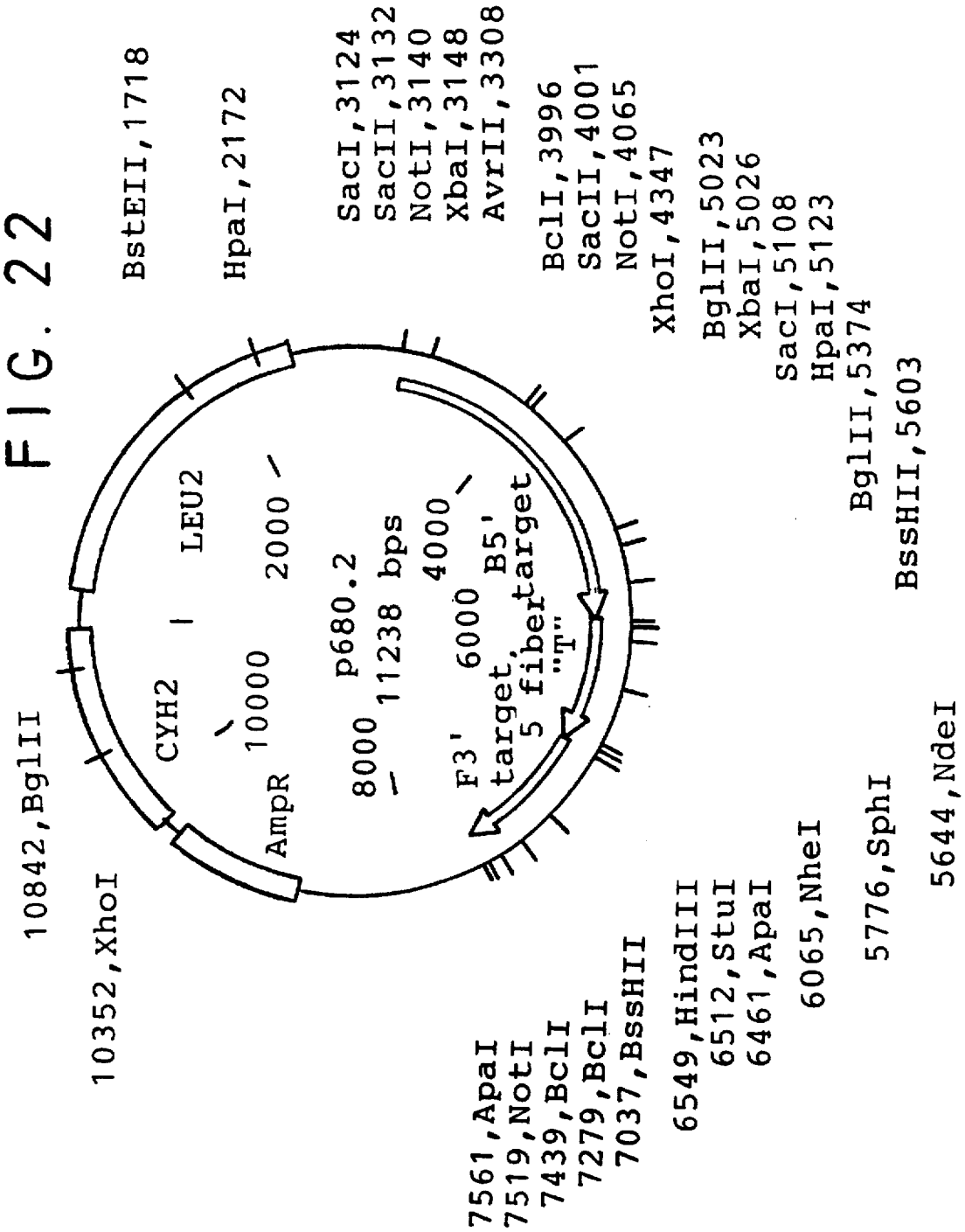
FIG. 22 is a map of plasmid p680.2.

The fragment was ligated into p680 digested with Apa I and Sal I to form p680.1. Second, the 3.4 kb Hind III to Xba I fragment containing the adenovirus 5 fiber tail and 5' flanking sequence was isolated from the 5,665 bp adenovirus 5 genomic Hind III "B" fragment. This fragment was ligated into p680.1 digested with Hind III and Xba I to form p680.2 as shown in FIG. 22.

The Adenovirus 5 fiber:CD30ligand (5T:CD30L) chimera is prepared by PCR gene overlap extension (Horton, et al., 1990). The Adenovirus 5 fiber tail and shaft, amino acids 1 to 400 will be connected with the extracellular domain of the CD30 ligand, amino acids 66 to 235. The primers which will be used in the PCR construction are as follows:

Adenovirus 5 fiber:
5'-CATTCTAGAATGAAGCGCGCAAGACCGTCT GAAGATA-3' (SEQ ID NO:17)
5'-GTCAGGTGAGTTGGGAATGGAGTCGGTCCA CAAAGTTAGCTTATCATT-5' (SEQ ID NO:18)

CD30 ligand:
5'-AATGATAAGCTAACTTTGTGGACCGACTCCA TTCCCAACTCACCTGAC-3' (SEQ ID NO:19)
5'-CATGAATTCTCAGTCTGAATTACTGTATAAG AAGATGGA-3' (SEQ ID NO:20)

Figure 23:
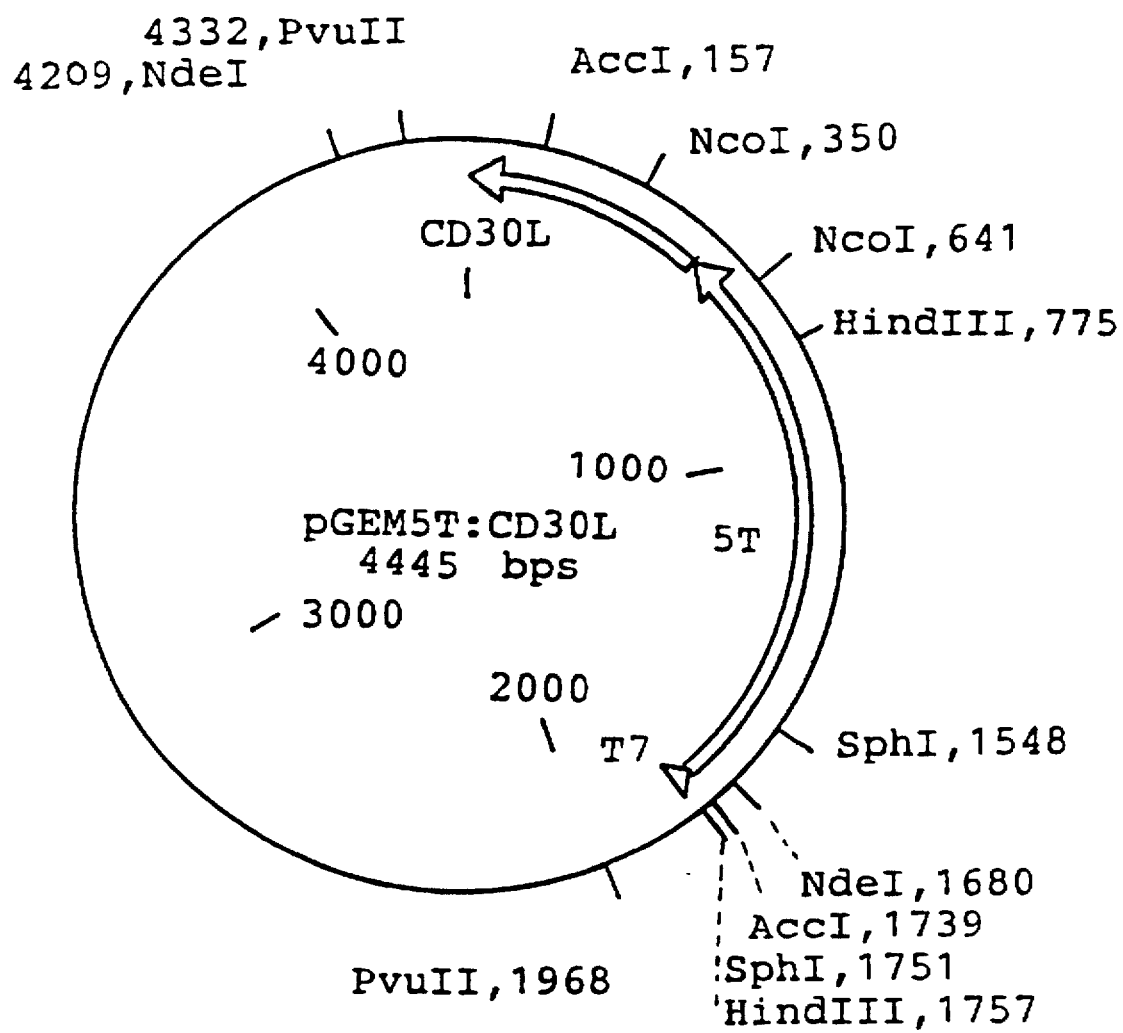
FIG. 23 is a map of plasmid pGEM5T: CD30L.

The Adenovirus 5 fiber primers amplify nucleotides 476 to 1684 of the Adenovirus 5 fiber sequence, Genbank #M18369. The CD30 ligand primers amplify nucleotides 310 to 819 of the CD30 ligand sequence, Genbank #L09753. The shorter Adenovirus 5 fiber primer and the shorter CD30 ligand primer are designed to add XbaI and EcoRI restriction enzyme sites, respectively, for cloning of the 1.7 kb5T:CD30L fragment into the expression vector, pGEM4Z (Promega) (FIG. 1) to form pGEM5T:CD30L. (FIG. 23.) The template pGEM5F (FIG. 2) which contains the correct cDNA for the Adenovirus 5 fiber gene is used to amplify the Adenovirus 5 tail and shaft regions. Human lymphocyte cDNA (Clonetech) is used as template for the amplification of the CD30L extracellular domain.

The fiber chimera is analyzed by expression in vitro and in baculovirus as described previously for the characterization of the 5T:TNF chimera described in Example 1.

Figure 24:
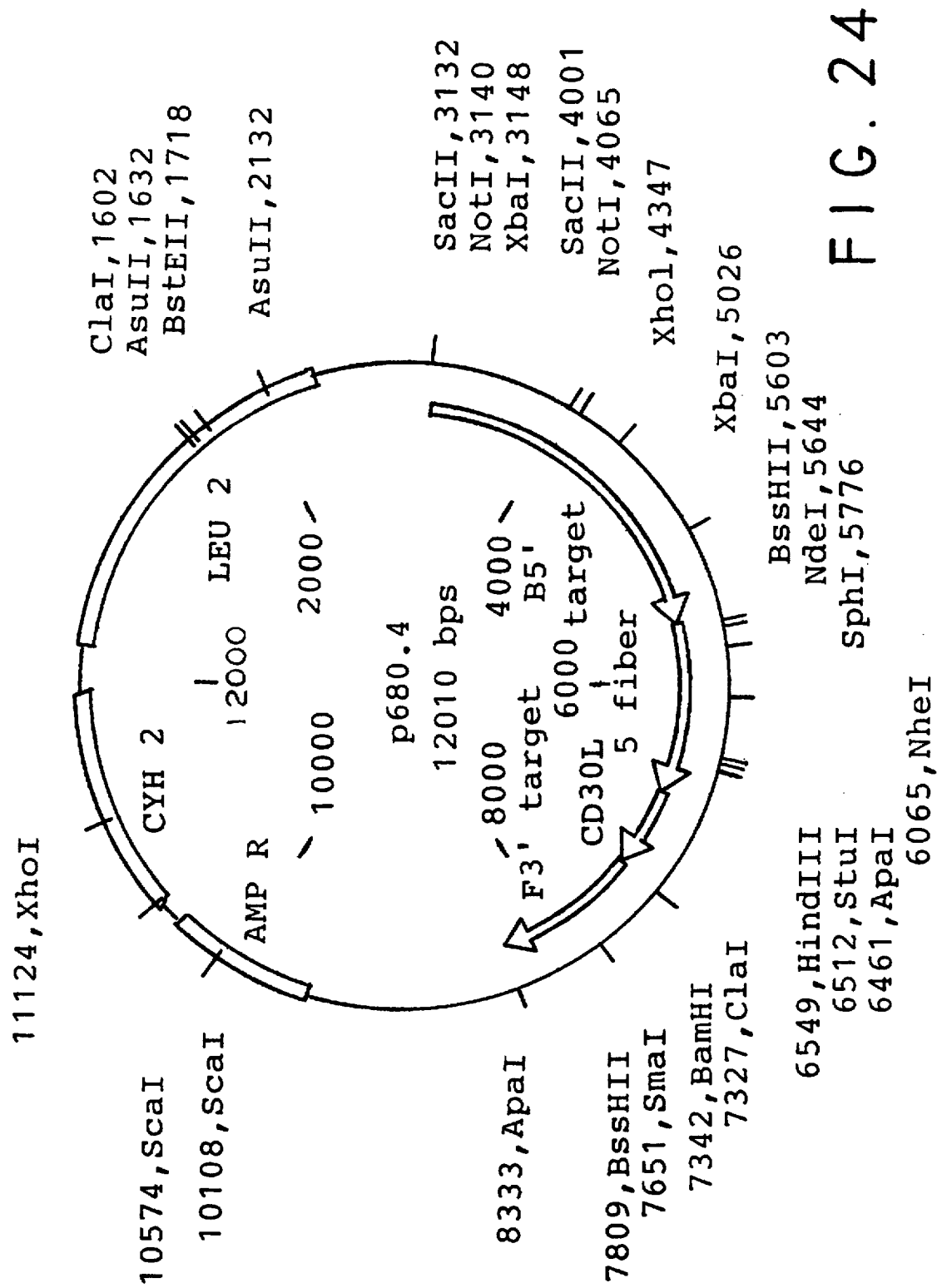
FIG. 24 is a map of plasmid p680.4.

The 5T:CD30L chimera is incorporated into an adenovirus using the YAC system. The CD30L extracellular domain is cloned into the YAC plasmid p680.2 to generate the plasmid p680.4. (FIG. 24.) The plasmid pGEM5T:CD30L is digested with EcoRI. The 5' overhangs then are filled in with the large fragment of DNA polymerase Klenow fragment, and then digested with HindIII for subsequent cloning into p680.2. The 533 bp CD30L fragment is cloned into p680.2 digested with HindIII to generate p680.4.

The p680.4 plasmid is used to derive a modified adenovirus genome using as a starting point a YAC containing the Adenovirus 5 genome or derivatives thereof using the method described by Ketner, et al., 1994.

In order to produce the adenoviral particle containing the CD30 ligand gene, the adenovirus genome is excised from the YAC by PacI digestion and the DNA is transfected into 293 cells which have been modified to express the CD30 receptor using calcium phosphate. Plaques are picked and used for amplification and for large scale production of the modified adenovirus. The receptor specificity of the modified adenovirus is tested using infectivity and competition analysis using the ligand.

Advantages of the present invention include the inclusion of a targeting ligand which replaces the natural binding ligand of the adenovirus, while retaining the trimeric structure of the fiber. This provides for the elimination of binding to the natural adenovirus receptor, and instead enables cell specific expression of the adenoviral DNA through binding of the modified adenoviral fiber to a targeted receptor on a desired cell type.

The disclosure of all patents, publications (including published patent applications), and database entries referenced in this specification are specifically incorporated herein by reference in their entirety to the same extent as if each such individual patent, publication, and database entry were specifically and individually indicated to be incorporated by reference.

It is to be understood, however, that the scope of the present invention is not to be limited to the specific embodiments described above. The invention may be practiced other than as particularly described and still be within the scope of the accompanying claims.

What is claimed is:

1. A method of expressing a therapeutic agent in an animal, comprising:

administering to an animal an adenovirus wherein the adenovirus fiber includes a ligand which is specific for a receptor located on a desired cell type, and wherein said adenovirus includes at least one DNA sequence encoding a therapeutic agent.

2. The method of claim 1 wherein said adenovirus is administered in an amount of from 1 plaque forming unit to about $10^{14}$ plaque forming units.

3. The method of claim 2 wherein said adenovirus is administered in an amount of from about $10^6$ plaque forming units to about $10^{13}$ plaque forming units.

4. The method of claim 1 wherein at least a portion of the adenovirus fiber protein is removed and replaced with a ligand which is specific for a receptor located on a desired cell type.

5. The method of claim 1 wherein said adenovirus includes a fusion protein of an adenovirus fiber protein and a ligand which is specific for a receptor located on a desired cell type.

6. A method of expressing a therapeutic agent in a eukaryotic cell, comprising:

transducing a eukaryotic cell with an adenovirus wherein the adenovirus fiber includes a ligand which is specific for a receptor located on a desired cell type, and wherein said adenovirus includes at least one DNA sequence encoding a therapeutic agent.

7. An adenovirus wherein at least a portion of the adenovirus fiber protein is removed and replaced with a ligand which is a member of the TNF superfamily of ligands.

8. The adenovirus of claim 7 wherein said ligand is lymphotoxin-$\alpha$.

9. The adenovirus of claim 7 wherein said ligand is lymphotoxin-$\beta$.

10. The adenovirus of claim 7 wherein said ligand is Fas ligand.

11. The adenovirus of claim 7 wherein said ligand is CD 27.

12. The adenovirus of claim 7 wherein said ligand is OX-40.

13. The adenovirus of claim 7 wherein said ligand is a CD30 ligand.

14. The adenovirus of claim 13 wherein said adenovirus further includes DNA encoding a negative selective marker.

* * * * *

SEQUENCE LISTING ( 1 ) GENERAL INFORMATION:

( i i i ) NUMBER OF SEQUENCES: 21

( 2 ) INFORMATION FOR SEQ ID NO: 1:

( i ) SEQUENCE CHARACTERISTICS:
        ( A ) LENGTH: 39 bases
        ( B ) TYPE: nucleic acid
        ( C ) STRANDEDNESS: single
        ( D ) TOPOLOGY: linear ( i i ) MOLECULE TYPE: PCR DNA primer ( x i ) SEQUENCE DESCRIPTION: SEQ ID NO: 1:

CATTGTGTCG ACACCATGAA GCGCGCAAGA CCGTCTGAA    39

( 2 ) INFORMATION FOR SEQ ID NO: 2:

( i ) SEQUENCE CHARACTERISTICS:
        ( A ) LENGTH: 48 bases
        ( B ) TYPE: nucleic acid
        ( C ) STRANDEDNESS: single
        ( D ) TOPOLOGY: linear ( i i ) MOLECULE TYPE: PCR DNA primer ( x i ) SEQUENCE DESCRIPTION: SEQ ID NO: 2:

CGGGGTTCGA GAAGATGATC TGACGGTCCA CAAAGTTAGC TTATCATT    48

( 2 ) INFORMATION FOR SEQ ID NO: 3:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: PCR DNA primer ( x i ) SEQUENCE DESCRIPTION: SEQ ID NO: 3:

GTCAGATCAT CTTCTCGAAC CCCG    24

( 2 ) INFORMATION FOR SEQ ID NO: 4:

( i ) SEQUENCE CHARACTERISTICS:
        ( A ) LENGTH: 39 bases
        ( B ) TYPE: nucleic acid ( C ) STRANDEDNESS: single
            ( D ) TOPOLOGY: linear ( i i ) MOLECULE TYPE: PCR DNA primer ( x i ) SEQUENCE DESCRIPTION: SEQ ID NO: 4:

ATGTCTAGAT CACAGGGCAA TGATCCCAAA GTAGACCTG                    39

( 2 ) INFORMATION FOR SEQ ID NO: 5:

( i ) SEQUENCE CHARACTERISTICS:
            ( A ) LENGTH: 38 bases
            ( B ) TYPE: nucleic acid
            ( C ) STRANDEDNESS: single
            ( D ) TOPOLOGY: linear ( i i ) MOLECULE TYPE: PCR DNA primer ( x i ) SEQUENCE DESCRIPTION: SEQ ID NO: 5:

CATCTGCAGC ATGAAGCGCG CAAGACCGTC TGAAGATA                     38

( 2 ) INFORMATION FOR SEQ ID NO: 6:

( i ) SEQUENCE CHARACTERISTICS:
            ( A ) LENGTH: 38 bases
            ( B ) TYPE: nucleic acid
            ( C ) STRANDEDNESS: single
            ( D ) TOPOLOGY: linear ( i i ) MOLECULE TYPE: PCR DNA primer ( x i ) SEQUENCE DESCRIPTION: SEQ ID NO: 6:

CAGGAATTCT TATTCTTGGG CAATGTATGA AAAAGTGT                     38

( 2 ) INFORMATION FOR SEQ ID NO: 7:

( i ) SEQUENCE CHARACTERISTICS:
            ( A ) LENGTH: 44 bases
            ( B ) TYPE: nucleic acid
            ( C ) STRANDEDNESS: single
            ( D ) TOPOLOGY: linear ( i i ) MOLECULE TYPE: PCR DNA primer ( x i ) SEQUENCE DESCRIPTION: SEQ ID NO: 7:

GCAGATCTTT CCGCAGCAGC CGCCACCATG AGCATGAAAG CATC              44

( 2 ) INFORMATION FOR SEQ ID NO: 8:

( i ) SEQUENCE CHARACTERISTICS:
            ( A ) LENGTH: 30 bases
            ( B ) TYPE: nucleic acid
            ( C ) STRANDEDNESS: single
            ( D ) TOPOLOGY: linear ( i i ) MOLECULE TYPE: PCR DNA primer ( x i ) SEQUENCE DESCRIPTION: SEQ ID NO: 8:

GCGTCGACTC GAGTCACAGG GCAATGATCC                              30

( 2 ) INFORMATION FOR SEQ ID NO: 9:

( i ) SEQUENCE CHARACTERISTICS:
            ( A ) LENGTH: 30 bases
            ( B ) TYPE: nucleic acid
            ( C ) STRANDEDNESS: single
            ( D ) TOPOLOGY: linear ( i i ) MOLECULE TYPE: PCR DNA primer ( x i ) SEQUENCE DESCRIPTION: SEQ ID NO: 9:

ATGGAGATCT TACTGAAGGC ACAGCCTATA  30

( 2 ) INFORMATION FOR SEQ ID NO: 10:

( i ) SEQUENCE CHARACTERISTICS:
        ( A ) LENGTH: 42 bases
        ( B ) TYPE: nucleic acid
        ( C ) STRANDEDNESS: single
        ( D ) TOPOLOGY: linear ( i i ) MOLECULE TYPE: PCR DNA primer ( x i ) SEQUENCE DESCRIPTION: SEQ ID NO: 10:

CCGCTTACGC AGCTTGCGCA GTTCTTGGGC AATGTATGAA AA  42

( 2 ) INFORMATION FOR SEQ ID NO: 11:

( i ) SEQUENCE CHARACTERISTICS:
        ( A ) LENGTH: 42 bases
        ( B ) TYPE: nucleic acid
        ( C ) STRANDEDNESS: single
        ( D ) TOPOLOGY: linear ( i i ) MOLECULE TYPE: PCR DNA primer ( x i ) SEQUENCE DESCRIPTION: SEQ ID NO: 11:

GTCATCGGCA TCGCGGAGGA GCCGCTTACG CAGCTTGCGC AG  42

( 2 ) INFORMATION FOR SEQ ID NO: 12:

( i ) SEQUENCE CHARACTERISTICS:
        ( A ) LENGTH: 42 bases
        ( B ) TYPE: nucleic acid
        ( C ) STRANDEDNESS: single
        ( D ) TOPOLOGY: linear ( i i ) MOLECULE TYPE: PCR DNA primer ( x i ) SEQUENCE DESCRIPTION: SEQ ID NO: 12:

CTTACGCAGC TTGCGCAGCA GGTCATCGGC ATCGCGGAGG AG  42

( 2 ) INFORMATION FOR SEQ ID NO: 13:

( i ) SEQUENCE CHARACTERISTICS:
        ( A ) LENGTH: 42 bases
        ( B ) TYPE: nucleic acid
        ( C ) STRANDEDNESS: single
        ( D ) TOPOLOGY: linear ( i i ) MOLECULE TYPE: PCR DNA primer ( x i ) SEQUENCE DESCRIPTION: SEQ ID NO: 13:

ATCTTCATCG CGGAGGAGCC GCTTACGCAG CTTGCGCAGC AG  42

( 2 ) INFORMATION FOR SEQ ID NO: 14:

( i ) SEQUENCE CHARACTERISTICS:
        ( A ) LENGTH: 42 bases
        ( B ) TYPE: nucleic acid
        ( C ) STRANDEDNESS: single
        ( D ) TOPOLOGY: linear ( i i ) MOLECULE TYPE: PCR DNA primer ( x i ) SEQUENCE DESCRIPTION: SEQ ID NO: 14:

TTAATGGAAT CCTTACAGGT CATCGGCATC GCGGAGGAGC CG  42

( 2 ) INFORMATION FOR SEQ ID NO: 15:

( i ) SEQUENCE CHARACTERISTICS:
        ( A ) LENGTH: 43 bases
        ( B ) TYPE: nucleic acid
        ( C ) STRANDEDNESS: single
        ( D ) TOPOLOGY: linear ( i i ) MOLECULE TYPE: PCR DNA primer ( x i ) SEQUENCE DESCRIPTION: SEQ ID NO: 15:

GGGCTCGAGG GATCCAGAAT CGTTTGTGTT ATGTTTCAAC GTG        43

( 2 ) INFORMATION FOR SEQ ID NO: 16:

( i ) SEQUENCE CHARACTERISTICS:
        ( A ) LENGTH: 37 bases
        ( B ) TYPE: nucleic acid
        ( C ) STRANDEDNESS: single
        ( D ) TOPOLOGY: linear ( i i ) MOLECULE TYPE: PCR DNA primer ( x i ) SEQUENCE DESCRIPTION: SEQ ID NO: 16:

CAAGGGCCCT GTGCCAACAT TGATATCATG ACGAGCA        37

( 2 ) INFORMATION FOR SEQ ID NO: 17:

( i ) SEQUENCE CHARACTERISTICS:
        ( A ) LENGTH: 37 bases
        ( B ) TYPE: nucleic acid
        ( C ) STRANDEDNESS: single
        ( D ) TOPOLOGY: linear ( i i ) MOLECULE TYPE: PCR DNA primer ( x i ) SEQUENCE DESCRIPTION: SEQ ID NO: 17:

CATTCTAGAA TGAAGCGCGC AAGACCGTCT GAAGATA        37

( 2 ) INFORMATION FOR SEQ ID NO: 18:

( i ) SEQUENCE CHARACTERISTICS:
        ( A ) LENGTH: 48 bases
        ( B ) TYPE: nucleic acid
        ( C ) STRANDEDNESS: single
        ( D ) TOPOLOGY: linear ( i i ) MOLECULE TYPE: PCR DNA primer ( x i ) SEQUENCE DESCRIPTION: SEQ ID NO: 18:

GTCAGGTGAG TTGGGAATGG AGTCGGTCCA CAAAGTTAGC TTATCATT        48

( 2 ) INFORMATION FOR SEQ ID NO: 19:

( i ) SEQUENCE CHARACTERISTICS:
        ( A ) LENGTH: 48 bases
        ( B ) TYPE: nucleic acid
        ( C ) STRANDEDNESS: single
        ( D ) TOPOLOGY: linear ( i i ) MOLECULE TYPE: PCR DNA primer ( x i ) SEQUENCE DESCRIPTION: SEQ ID NO: 19:

AATGATAAGC TAACTTTGTG GACCGACTCC ATTCCCAACT CACCTGAC        48

( 2 ) INFORMATION FOR SEQ ID NO: 20:

( i ) SEQUENCE CHARACTERISTICS:
        ( A ) LENGTH: 39 bases
        ( B ) TYPE: nucleic acid ( C ) STRANDEDNESS: single
( D ) TOPOLOGY: linear ( i i ) MOLECULE TYPE: PCR DNA primer ( x i ) SEQUENCE DESCRIPTION: SEQ ID NO: 20:

CATGAATTCT CAGTCTGAAT TACTGTATAA GAAGATGGA    39

( 2 ) INFORMATION FOR SEQ ID NO: 21:

( i ) SEQUENCE CHARACTERISTICS:
( A ) LENGTH: 1548 bases
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: Factor IX cDNA ( x i ) SEQUENCE DESCRIPTION: SEQ ID NO: 21:

| | | | | | |
|---|---|---|---|---|---|
| AGGTTATGCA | GCGCGTGAAC | ATGATCATGG | CAGAATCACC | AGGCCTCATC | ACCATCTGCC | 60 |
| TTTTAGGATA | TCTACTCAGT | GCTGAATGTA | CAGTTTTCT | TGATCATGAA | AACGCCAACA | 120 |
| AAATTCTGAA | TCGGCCAAAG | AGGTATAATT | CAGGTAAATT | GGAAGAGTTT | GTTCAAGGGA | 180 |
| ACCTTGAGAG | AGAATGTATG | GAAGAAAGT | GTAGTTTTGA | AGAAGCACGA | GAAGTTTTTG | 240 |
| AAAACACTGA | AGAACAACT | GAATTTTGGA | AGCAGTATGT | TGATGGAGAT | CAGTGTGAGT | 300 |
| CCAATCCATG | TTTAAATGGC | GGCAGTTGCA | AGGATGACAT | TAATTCCTAT | GAATGTTGGT | 360 |
| GTCCCTTTGG | ATTTGAAGGA | AAGAACTGTG | AATTAGATGT | AACATGTAAC | ATTAAGAATG | 420 |
| GCAGATGCGA | GCAGTTTTGT | AAAAATAGTG | CTGATAACAA | GGTGGTTTGC | TCCTGTACTG | 480 |
| AGGGATATCG | ACTTGCAGAA | AACCAGAAGT | CCTGTGAACC | AGCAGTGCCA | TTTCCATGTG | 540 |
| GAAGAGTTTC | TGTTTCACAA | ACTTCTAAGC | TCACCCGTGC | TGAGACTGTT | TTTCCTGATG | 600 |
| TGGACTATGT | AAATTCTACT | GAAGCTGAAA | CCATTTTGGA | TAACATCACT | CAAAGCACCC | 660 |
| AATCATTTAA | TGACTTCACT | CGGGTTGTTG | GTGGAGAAGA | TGCCAAACCA | GGTCAATTCC | 720 |
| CTTGGCAGGT | TGTTTTGAAT | GGTAAAGTTG | ATGCATTCTG | TGGAGGCTCT | ATCGTTAATG | 780 |
| AAAAATGGAT | TGTAACTGCT | GCCCACTGTG | TTGAAACTGG | TGTTAAAATT | ACAGTTGTCG | 840 |
| CAGGTGAACA | TAATATTGAG | GAGACAGAAC | ATACAGAGCA | AAAGCGAAAT | GTGATTCGAA | 900 |
| TTATTCCTCA | CCACAACTAC | AATGCAGCTA | TTAATAAGTA | CAACCATGAC | ATTGCCCTTC | 960 |
| TGGAACTGGA | CGAACCCTTA | GTGCTAAACA | GCTACGTTAC | ACCTATTTGC | ATTGCTGACA | 1020 |
| AGGAATACAC | GAACATCTTC | CTCAAATTTG | GATCTGGCTA | TGTAAGTGGC | TGGGGAAGAG | 1080 |
| TCTTCCACAA | AGGGAGATCA | GCTTTAGTTC | TTCAGTACCT | TAGAGTTCCA | CTTGTTGACC | 1140 |
| GAGCCACATG | TCTTCGATCT | ACAAAGTTCA | CCATCTATTA | CAACATGTTC | TGTGCTGGCT | 1200 |
| TCCATGAAGG | AGGTAGAGAT | TCATGTCAAG | GAGATAGTGG | GGGACCCCAT | GTTACTGAAG | 1260 |
| TGGAAGGGAC | CAGTTTCTTA | ACTGGAATTA | TTAGCTGGGG | TGAAGAGTGT | GCAATGAAAG | 1320 |
| GCAAATATGG | AATATATACC | AAGGTATCCC | GGTATGTCAA | CTGGATTAAG | GAAAAAACAA | 1380 |
| AGCTCACTTA | ATGAAAGATG | GATTTCCAAG | GTTAATTCAT | GGAATTGAA | AATTAACAGG | 1440 |
| GCCTCTCACT | AACTAATCAC | TTTCCCATCT | TTGTTAGAT | TGAATATAT | ACATTCTATG | 1500 |
| ATCATTGCTT | TTTCTCTTTA | CAGGGGAGAA | TTTCATATTT | TACCTGAG | | 1548 |